(12) United States Patent
Gonzalez Garcia et al.

(10) Patent No.: US 12,288,617 B2
(45) Date of Patent: Apr. 29, 2025

(54) SPLIT VISION VISUAL TEST

(71) Applicant: OLLEYES, INC., Summit, NJ (US)

(72) Inventors: Alberto O. Gonzalez Garcia, Miami, FL (US); Freddy Salomon Morgenstern, Wayne, PA (US)

(73) Assignee: OLLEYES, INC., Summit, NJ (US)

( * ) Notice: Subject to any disclaimer, the term of this patent is extended or adjusted under 35 U.S.C. 154(b) by 284 days.

(21) Appl. No.: 17/487,479

(22) Filed: Sep. 28, 2021

(65) Prior Publication Data

US 2022/0013228 A1 Jan. 13, 2022

Related U.S. Application Data

(63) Continuation-in-part of application No. PCT/US2021/015694, filed on Jan. 29, 2021.

(60) Provisional application No. 62/968,215, filed on Jan. 31, 2020.

(51) Int. Cl.
| | |
|---|---|
| G06F 3/147 | (2006.01) |
| A61B 3/00 | (2006.01) |
| A61B 3/18 | (2006.01) |
| G06F 1/16 | (2006.01) |
| G06F 3/01 | (2006.01) |
| G06F 3/16 | (2006.01) |
| G16H 40/63 | (2018.01) |

(52) U.S. Cl.
CPC ........... *G16H 40/63* (2018.01); *A61B 3/0025* (2013.01); *A61B 3/005* (2013.01); *A61B 3/18* (2013.01); *G06F 1/163* (2013.01); *G06F 3/013* (2013.01); *G06F 3/167* (2013.01)

(58) Field of Classification Search
CPC ...... G16H 40/63; A61B 3/0025; A61B 3/005; A61B 3/18; G06F 1/163; G06F 3/013; G06F 3/167
See application file for complete search history.

(56) References Cited

U.S. PATENT DOCUMENTS

| | | | |
|---|---|---|---|
| 2019/0110754 A1* | 4/2019 | Rao | G06N 7/00 |
| 2019/0150727 A1* | 5/2019 | Blaha | A61B 3/0033 |
| 2019/0222817 A1* | 7/2019 | Abou Shousha | H04N 9/646 |
| 2019/0298166 A1* | 10/2019 | Smith | A61B 3/0091 |

(Continued)

OTHER PUBLICATIONS

International Search Report and Written Opinion of corresponding PCT/US21/15694, mailed on Apr. 14, 2021.

*Primary Examiner* — Jonathan Ng
*Assistant Examiner* — Benjamin L. Hanks

(57) ABSTRACT

Embodiments of the invention are directed towards systems, methods and computer program products for providing improved eye tests. Such tests improve upon current eye tests, such as visual acuity tests, by incorporating virtual reality, software mediated guidance to the patient or practitioner such that more accurate results of the eye tests are obtained. Furthermore, through the use of one or more trained machine learning or predictive analytic systems, multiple signals obtained from sensors of a testing apparatus are evaluated to ensure that the eye test results are less error-prone and provide a more consistent evaluation of a user's vision status. As it will be appreciated, such error reduction and user guidance systems represent technological improvements in eye tests and utilize non-routine and non-conventional approaches to the improvement and reliability of eye tests.

17 Claims, 16 Drawing Sheets

(56) References Cited

U.S. PATENT DOCUMENTS

2022/0400943 A1* 12/2022 Lee .................. A61B 3/102
2023/0225609 A1    7/2023 Gonzalez Garcia et al.

* cited by examiner

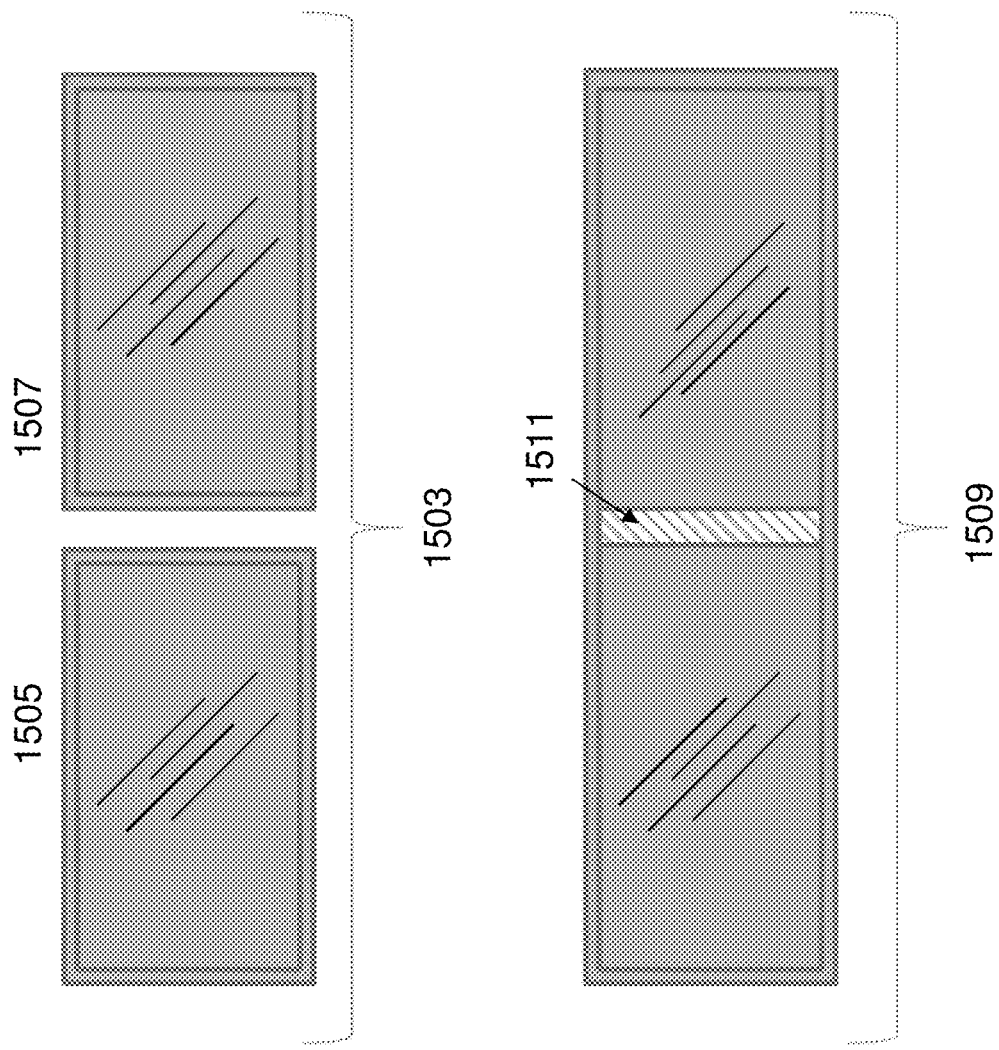

SPLIT VISION VISUAL TEST

CROSS-REFERENCE TO RELATED APPLICATIONS

This application is a Continuation in part of International application PCT/US2021/015694, filed Jan. 29, 2021, which claims priority to U.S. Provisional Patent Application Ser. No. 62/968,215, filed Jan. 31, 2020.

FIELD OF THE INVENTION

The invention generally relates to systems and methods for the testing the eye of a subject. More particularly, the invention relates to a system and method for performing visual acuity test, contrast sensitivity test, color vision test, visual field test, tonometry, ophthalmic photography, gaze alignment test, light adaptometry test, pupillometry, autorefraction and vision therapy on a subject.

BACKGROUND OF THE INVENTION

Eye testing, such as visual acuity testing, are common approaches to measuring a subject's vision. For instance, visual acuity testing (VA) is concerned with measuring the acuteness or clearness of a subject's vision. A VA test is one that is specifically designed to measure a subject's dynamic visual acuity and concentrates on the subject's ability to visually discern fine details in an object while of the head of the subject is being displaced at a generally constant velocity. A different test, gaze stabilization, focuses on the ability of a subject to ascertain details of an object while his or her head is being displaced over a range of different velocities. Visual Field tests are usually carried out by a health care professional. However, scheduling an appointment for such a test is time consuming. Instead there is a need and a desire for some users to conduct self-assessments of their visual field and other eye tests. Prior approaches of self-administered eye tests are prone to errors and problems with repeatably. Thus, one of the needs in the art is to provide a more robust guidance system for conducting eye test assessments. Furthermore, what is needed in the art are systems, platforms and apparatus that incorporate one or more machine learning or other predictive analytics to ensure error free eye assessments.

SUMMARY OF THE INVENTION

Embodiments of the invention are directed towards systems, methods and computer program products for providing improved eye tests. Such tests improve upon current eye tests, such as visual acuity tests, by incorporating virtual reality, software mediated guidance to the patient or practitioner such that more accurate results of the eye tests are obtained. Furthermore, through the use of one or more trained machine learning or predictive analytic systems, multiple signals obtained from sensors of a testing apparatus are evaluated to ensure that the eye test results are less error-prone and provide a more consistent evaluation of a user's vision status. As it will be appreciated, such error reduction and user guidance systems represent technological improvements in eye tests and utilize non-routine and non-conventional approaches to the improvement and reliability of eye tests.

In a further implementation, the present invention is directed to one or more visual test devices, where the visual field test session provided by the visual test device is configured to provide, simultaneously, each eye of the test subject with a fixation target. In one particular configuration, the visual test device is configured to use a single screen with a divider or septum between the eyes or separate independent screens for each eye. In this configuration, each screen or divided portion of a single screen provides a fixation target for the patient. The patient perceives both fixation targets as a single visual target as the human brain tends to fuse both fixation targets that are presented at a given position.

The inventors have determined that performing the visual field test with both eyes open and fixating at a fused fixation target represents a significant advantage over existing visual field tests. For instance, by using a fused image (separate images provided for both eyes), the results of the visual field test are highly reproducible. Such reproducibility is present even in tests administered to a patient having an eye with a seco central scotoma, where the fellow eye has good fixation.

For example, in a particular implementation, the present apparatus, systems and computer implemented methods described herein are utilized to provide an improved visual field test using a virtual, augmented and mixed reality goggles configured to provide a visual test, where the virtual, augmented and mixed reality goggles include a screen divided in two halves by a septum or a set of two screens. In a further implementation, the virtual, augmented and mixed reality goggles includes at least one subject sensor configured to monitor the subject during administration of the visual test and at least one data processor and at least one memory storage device. In the provided configuration, at least one sensor disposed within the goggles, wherein at least one sensor is configured to track the eye-movements of the subject.

In a further implementation, the improved visual field test apparatus having a screen divided in two halves by a septum or a set of two screens is configured by one or more processors thereof to display a fixation target on both screens where both eye can see it as one; the processor further configured to provide a set of n stimuli, wherein n is greater than or equal to 2, each stimulus having a (a) specified size, (b) shape and (c) luminance, wherein the luminance of the stimulus is greater than the luminance of a background; provide a set of n stimuli alternating randomly between right and left eye while keeping fixation on both fixation targets seen as one; receive from the patient at least one response when the patient views at least one stimulus; repeat steps (ii) to (vi) at least y times, where y is greater than 2, until the patient indicates that the lowest stimulus intensity has been seen; calculate a visual field score if a percentage of responses in step (vii) labeled as correct is greater than or equal to the percentage expected to be correct based on a historical value for the patient's retinal sensitivity score or an estimated percentage of correct choices based on a probability score.

In one particular implementation the present apparatus, systems and computer implemented methods described herein are utilized to provide an improved visual acuity test, the improved visual acuity test comprising, at least one data processor comprising a virtual reality engine and at least one memory storing instruction which is executed by at least one data processor, at least one data processor configured to: (i) present a virtual assistant in virtual reality, wherein the virtual assistant presents to a patient a set of instructions for the visual acuity test, (ii) provide a set of n optotypes, wherein n is greater than or equal to 2, each optotype having a (a) specified size, (b) shape and (c) luminance, wherein the luminance of the optotypes is greater or lower than the luminance of a background. In a further implementation, the system described is configured to (iii) receive from the patient at least one response when the patient views at least one optotype, wherein the response comprises selection of a position of the at least one optotype or location of an arrow associated with the at least one optotype. Using this information, (iv) the system described repeat steps (ii) to iii) at least y times, where y is greater than 2, until the patient indicates that he/she cannot identify any optotypes having a size smaller than the last optotype the patient responded to in step (iii) and (v) repeat steps (i) to (iv), wherein the explanation in step (i) is modified based on the patient's response to provide a second set of instructions selected from a library instructions if a percentage of responses in step (iii) labeled as correct is less than the percentage expected to be correct based on a historical value for the patient's visual acuity score or an estimated percentage of correct choices based on a probability score; or (vi) calculate a visual acuity score if a percentage of responses in step (iii) labeled as correct is greater than or equal to the percentage expected to be correct based on a historical value for the patient's visual acuity score or an estimated percentage of correct choices based on a probability score.

The present description is also directed to a system for evaluating an in progress visual field test of an individual, the system comprising a training database, wherein the training database includes, for each member of a training population comprised of users of a visual acuity test, an assessment dataset that includes at least data relating to a respective user data obtained during a visual field test and a visual field outcome data value corresponding to the respective member. The training system includes an expert system module configured to determine correlations between the respective user data obtained during a visual field test and the visual field outcome data values each member of the training population; and a user testing platform configured to provide a user with a current visual field test and receive user data during administration of the test. The described system further includes an analysis system communicatively coupled to the training system and the user testing platform, the computer system adapted to receive the user data generated during administration of the visual field test in response to the current visual field test and to determine if an error has been made using the correlations obtained from the training system.

BRIEF DESCRIPTION OF THE DRAWINGS

Embodiments of the invention are illustrated in the figures of the accompanying drawings which are meant to be exemplary and not limiting, in which like references are intended to refer to like or corresponding parts, and in which:

FIGS. 16A and 16B present a component diagram illustrating the configurations of the display device.

DETAILED DESCRIPTION OF CERTAIN EMBODIMENTS OF THE INVENTION

By way of overview, various embodiments of the systems, methods and computer program products described herein are directed towards devices to conduct improved eye tests. Furthermore, in one or more particular implementations, the visual field testing devices described herein are configured to enable a user (such as a patient) to self-administer the visual field test. In this manner, the user is freed from the time and costs associated with scheduling and physically visiting a physician or medical facility to obtain visual field test. In one or more implementations of the systems, apparatus and computer program products described herein, the improved platform for administering visual field tests includes providing an altered field of vision device to a user that that incorporates one or more virtual software agents that provide step-by-step guidance to the user (such as a patient or practitioner) such that the results of the visual field tests are accurate and reliable. Furthermore, through the use of one or more trained machine learning based systems, the results of a field of view based visual acuity test are interpreted so as to provide more accurate measurements of a patient's current visual state by avoiding or reducing measurement errors. Furthermore, such machine learning systems improve the overall experience of a user such that the visual field test is more streamlined, informative, less stressful and able to produce more consistent results. Such systems and approaches described herein represent improvements in the technological art of visual field testing through the use of non-routine and non-conventional approaches that improve the functionating of visual field testing platforms.

Various objects, features, aspects and advantages of the subject matter described herein will become more apparent from the following detailed description of particular implementations, along with the accompanying drawing figures in which like numerals represent like components.

Figure 1:
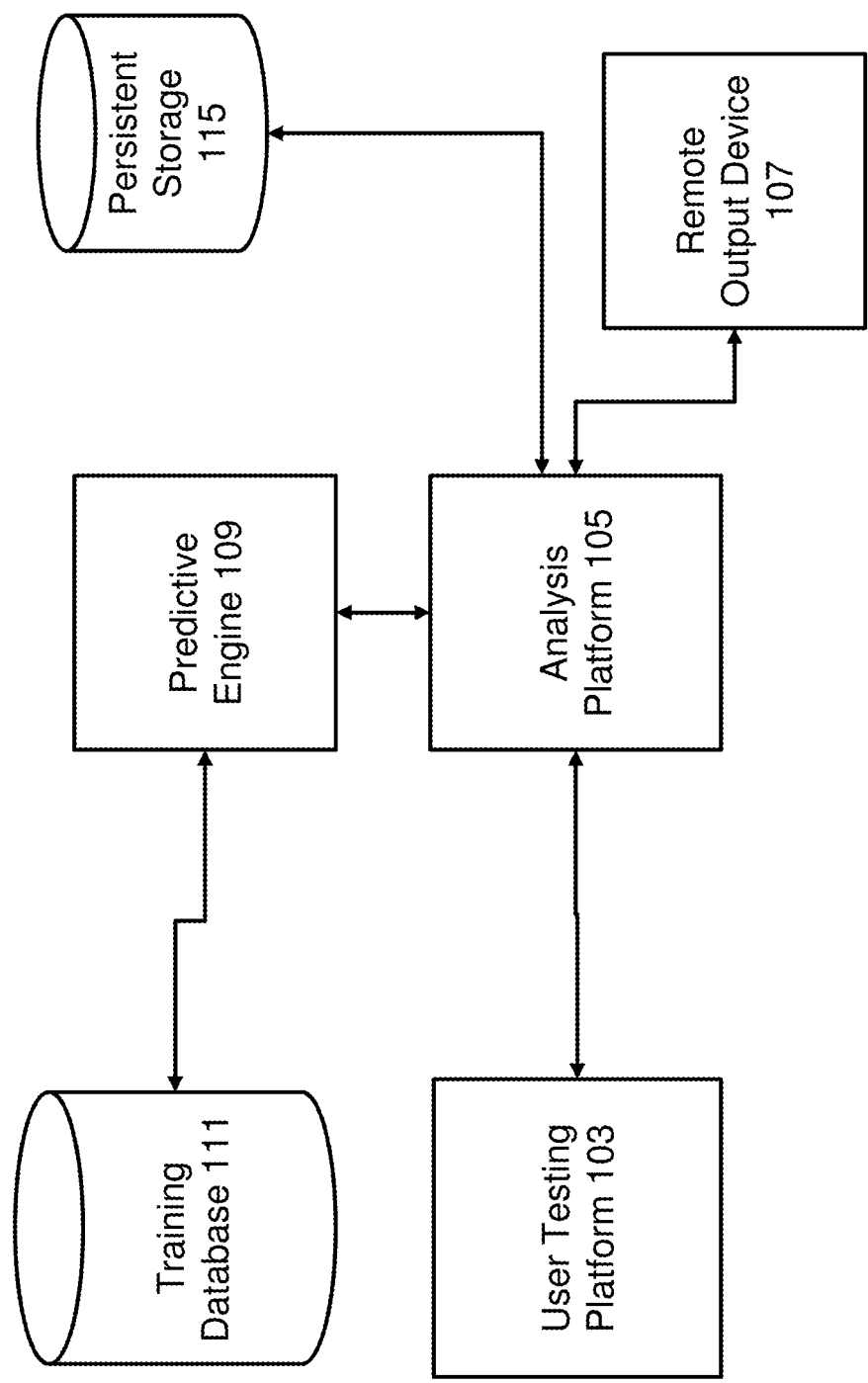
FIG. 1 illustrates a block diagram of a system for implementing visual field and other eye tests according to one embodiment of the present invention.

As shown with respect to FIG. 1, an eye testing platform system and method is provided. Here, one or more components or devices are linked, connected, networked or otherwise interfaced with one another (shown in solid lines) such that data generated or residing on one or more of the components can be passed or exchanged to a different component. For example, bi-directional data transfers are indicated by the solid lines connecting each of the labeled components provided in FIG. 1.

The eye testing platform system provided in FIG. 1 includes, in one implementation, a user testing platform 103. The user testing platform 103 is configured to receive user input data from a user in response to carrying out a visual filed test. For example, and in no way limiting, the user testing platform 103 is a virtual reality (VR) or augment reality (AR) device the provides a mediated field of view to a user. For example, a user may wear a pair of goggles, glasses, a monocle or other display device that allows for a display to be presented to a user where such a display provides a semi- or completely virtual visual environment to the user. By way of further example, such a display incorporated into a user testing platform 103 is configured to generate one or more icons, graphics, graphical user interfaces or computer-generated imagery is provided to the wearer or user.

In one particular implementation, the user testing platform includes a virtual, augmented and mixed reality goggles configured to provide a visual test, where the virtual, augmented and mixed reality goggles include a screen divided in two halves by a septum or a set of two screens.

Figure 9:
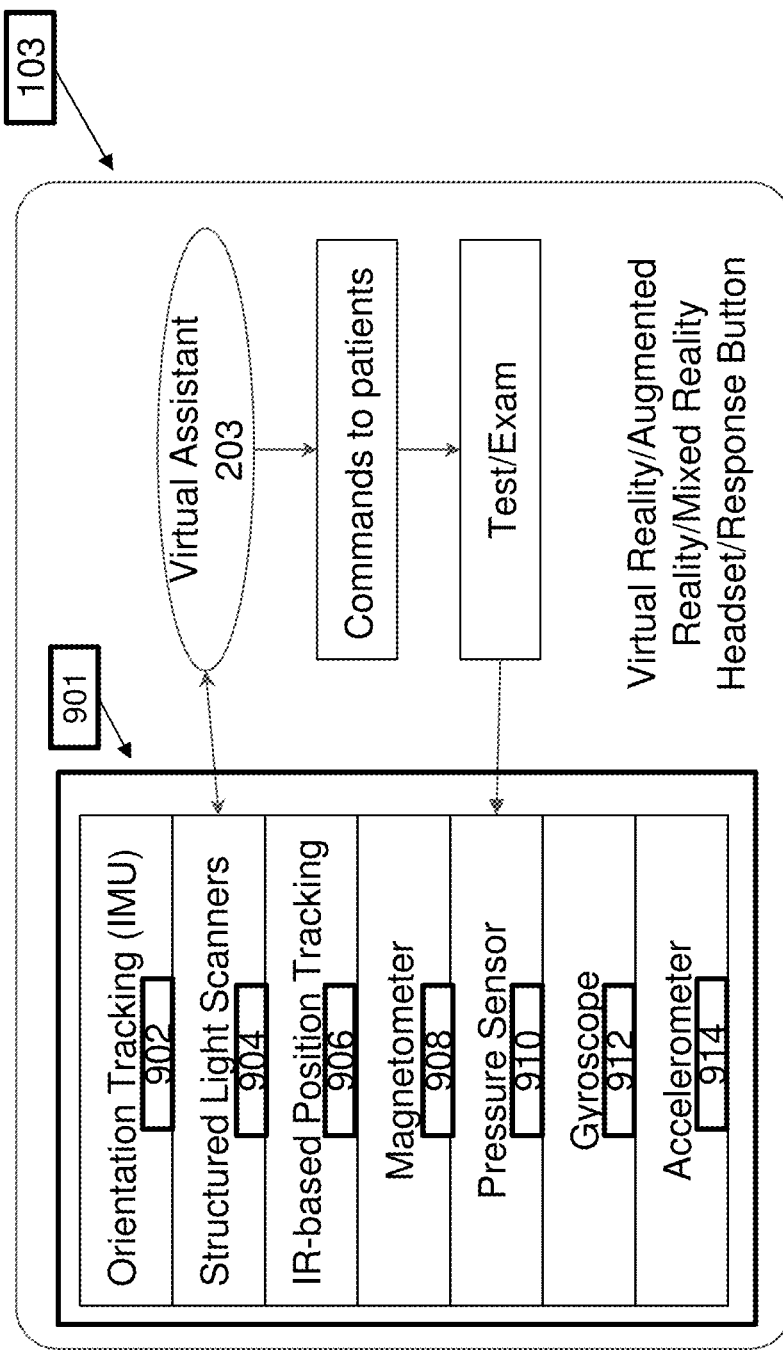
FIG. 9 presents a component diagram illustrating components and sensors of an eye testing device for use in accordance with one embodiment of the present invention.

Turning briefly to FIG. 9, the user testing platform 103 includes, in one or more implementations, such as sensors 901, that are utilized to capture user input as well as the position and movement of a user or wearer of the user testing platform 103. For example, the user testing platform 103 is configured with a display, a user testing platform (such as a control interface or buttons). In one or more implementations, the user testing platform 103 includes a screen, monitor, display, LED, LCD or OLED panel, augmented or virtual reality interface or an electronic ink-based display device that provides the visual display to the wearer. For example, with particular reference to FIGS. 16A and 16B, alternative configurations of the virtual, augmented and mixed reality goggles configured are provided. As shown, in one configuration provided in FIG. 16A, the virtual, augmented and mixed reality goggles include a screen 1503 configured to provide a visual test. Here, the screen is composed of two display panels 1505 and 1507, each configured to display the same information to each eye of the wearer.

In an alternative configuration, shown in FIG. 16B, the virtual, augmented and mixed reality goggles include a screen 1509 configured to provide a visual test. Here, the screen 1509 is composed of a single display panel. A baffle, septum or divider 1511 is provided in the center of the screen 1509 that restricts the view presented to each eye of the wearer.

It will be appreciated that in the foregoing disclosure, the content provided to each individual portion of the screen 1509 or the individual display panels 1505 and 1507, is controlled by the processor. As such, where the following disclosure describes presenting visual information to the user, such visual information is presented on both sides of the single display panel 1509 or on each independent display panel.

Furthermore, the user testing platform 103 includes and one or more orientation tracking units 902, structured light scanners 904, IR position trackers 906, magnetometers 908, pressure sensors 910, gyroscopes 912, accelerometers 914, as well as the necessary power supplies and data storage memories and associated components to implement such displays and sensors. In one or more implementations, these sensor devices are configured to output data to one or more local or remote data processing devices, processors or computers. For example, a data processor configured to receive data from an orientation tracking unit 902 can be further configured to adjust or update a graphical element that is being displayed to a user so as to simulate movement or repositioning of that element while taking into account the user's own movements. The data gathered by the user testing platform 103 can be packaged and uploaded to a persistent data store, which may be local or remote to the control device, e.g., to serve as supporting data with regard to the safety or efficacy of a particular self-administered visual field test.

Returning to FIG. 1, the output of the user testing platform 103 is provided to an analysis platform 105. Such output can be provided though a wired or wireless connection. For example, data obtained by the user testing platform 103 is transmitted via RF signal to a receiver associated with the analysis platform 105. Here, the analysis platform 105 is configured to access live and/or recorded data from the user testing platform 103 and use that data to instruct a user to carry out a self-administered visual field test or instruct a health care professional how to manage a user operating the user testing platform.

In one or more implementations, the analysis platform 105 includes one or more processors or computer elements. For example, a processor when used generally throughout, and not exclusively when referring to the analysis platform, can be a computer or discrete computing element such as microprocessor. In one or more particular implementations, the processor is incorporated into one a desktop or workstation class computer that executes a commercially available operating system, e.g., MICROSOFT WINDOWS, APPLE OSX, UNIX or Linux based operating system implementations. In another implementation, the processors or computers of the analysis platform 105 are located or configured as a cloud or remote computing cluster made of multiple discrete computing elements, such as servers. Such a cloud computing cluster is available on an as needed basis and can provide a pre-determined level of computing power and resources. In accordance with alternative embodiments, the processors or computer of the analysis platform 105 can be a portable computing device such as a smartphone, wearable or tablet class device. For example, analysis platform 105 is an APPLE IPAD/IPHONE mobile device, ANDROID mobile device or other commercially available mobile electronic device configured to carry out the processes described herein. In other embodiments, the analysis platform 105 comprises custom or non-standard hardware configurations. For instance, the analysis platform 105 may comprise one or more micro-computer(s) operating alone or in concert within a collection of such devices, network adaptors and interfaces(s) operating in a distributed, but cooperative, manner, or array of other micro-computing elements, computer-on-chip(s), prototyping devices, "hobby" computing elements, home entertainment consoles and/or other hardware.

The analysis platform 105 and user testing platform 103 can be equipped or be in communication with a persistent memory (not shown) that is operative to store the operating system or the relevant computer or processor in addition to one or more additional software modules, such as those described herein that relate to implementing visual tests and providing for virtual assistant functionality in accordance with embodiments described herein. In one or more implementations, the persistent memory includes read only memory (ROM) and/or a random-access memory (e.g., a RAM). Such computer memories may also comprise secondary computer memory, such as magnetic or optical disk drives or flash memory, that provide long term storage of data in a manner similar to the persistent storage. In accordance with one or more embodiments, the memory comprises one or more volatile and non-volatile memories, such as Programmable Read Only-Memory ("PROM"), Erasable Programmable Read-Only Memory ("EPROM"), Electrically Erasable Programmable Read-Only Memory ("EEPROM"), Phase Change Memory ("PCM"), Single In-line Memory ("SIMM"), Dual In-line Memory ("DIMM") or other memory types. Such memories can be fixed or removable, as is known to those of ordinary skill in the art, such as through the use of removable media cards or similar hardware modules. In one or more embodiments, the memory of the analysis platform 105 and or the user testing platform 103 provides for storage of application program and data files when needed by a processor or computer. One or more read-only memories provide program code that the processor or computer of the analysis platform 105 or the user testing platform 103 reads and implements at startup or initialization, which may instruct a processor associated therewith to execute specific program code from the persistent storage device to load into RAM at startup.

In one embodiment provided herein, the modules stored in memory utilized by the analysis platform 105 comprise software program code and data that are executed or otherwise used by one or more processors integral or associated with the analysis platform 105 thereby causing the analysis platform 105 to perform various actions dictated by the software code of the various modules. For instance, the analysis platform 105 is configured with one or more processors that are configured to execute code. Here, the code includes a set of instructions for evaluating and providing data to and from the user testing platform 103.

Building on the prior example, the analysis platform 105 at startup retrieves initial instructions from ROM as to initialization of one or more processors. Upon initialization, program code that the processor retrieves and executes from ROM instructs the processor to retrieve and begin execution of virtual assistant application program code. The processor begins execution of the virtual assistant application program code, loading appropriate program code to run into RAM and presents a user interface to the user that provides access to one or more functions that the program code offers. According to one embodiment, the virtual assistant application program code presents a main menu after initialization that allows for the creation or modification of the user's desired avatar, testing plans, prior test results, and other information or protocols that are relevant to a user. While reference is made to code executing in the processor, it should be understood that the code can be executed or interpreted or comprise scripts that are used by the processor to implement prescribed routines.

In accordance with certain embodiments, the analysis platform 105 is also in communication with a persistent data store 115 that is located remote from the remote persistent data store 115 such that the analysis platform 105 is able to access the remote persistent data store 115 over a computer network, e.g., the Internet, via a network interface, which implements communication frameworks and protocols that are well known to those of skill in the art.

In one configuration, the database 115 is connected to the analysis platform 105 via a server or network interface and provides additional storage or access to user data, community data, or general-purpose files or information. The physical structure of the database 115 may be embodied as solid-state memory (e.g., ROM), hard disk drive systems, RAID, disk arrays, storage area networks ("SAN"), network attached storage ("NAS") and/or any other suitable system for storing computer data. In addition, the database 115 may comprise caches, including database caches and/or web caches. Programmatically, the database 115 may comprise flat-file data store, a relational database, an object-oriented database, a hybrid relational-object database, a key-value data store such as HADOOP or MONGODB, in addition to other systems for the structure and retrieval of data that are well known to those of skill in the art.

In addition to a persistent storage device 115, the analysis platform 105 may connect to one or more remote computing devices 107. Such computing devices are configured to exchange data with the analysis platform 105.

In a further implementation, the present invention is directed to one or more visual test devices, where the visual field test session provided by the visual test device is configured to provide, simultaneously, each eye of the test subject with a fixation target. In one particular configuration, the visual test device is configured to use a single screen with a divider or septum between the eyes or separate independent screens for each eye. In this configuration, each screen or divided portion of a single screen provides a fixation target for the patient. The patient perceives both fixation targets as a single visual target as the human brain tends to fuse both fixation targets that are presented at a given position.

The inventors have determined that performing the visual field test with both eyes open and fixating at a fused fixation target represents a significant advantage over existing visual field tests. For instance, by using a fused image (separate images provided for both eyes), the results of the visual field test are highly reproducible. Such reproducibility is present even in tests administered to a patient having an eye with a seco central scotoma, where the fellow eye has good fixation.

For example, in a particular implementation, the present apparatus, systems and computer implemented methods described herein are utilized to provide an improved visual field test using a virtual, augmented and mixed reality goggles configured to provide a visual test, where the virtual, augmented and mixed reality goggles include a screen divided in two halves by a septum or a set of two screens. In a further implementation, the virtual, augmented and mixed reality goggles include at least one subject sensor configured to monitor the subject during administration of the visual test and at least one data processor and at least one memory storage device. In the provided configuration, at least one sensor disposed within the goggles, wherein at least one sensor is configured to track the eye-movements of the subject.

In a further implementation, the improved visual field test apparatus having a screen divided in two halves by a septum or a set of two screens is configured by one or more processors thereof to display a fixation target on both screens where both eye can see it as one; the processor further configured to provide a set of n stimuli, wherein n is greater than or equal to 2. In the provided configuration, each stimulus has a (a) specified size, (b) shape and (c) luminance, wherein the luminance of the stimulus is greater than the luminance of a background.

The processor is further configured to provide a set of n stimuli alternating randomly between right and left eye while keeping fixation on both fixation targets seen as one. Additionally, the processor is configured to receive from the patient at least one response when the patient views at least one stimulus. Here, the processor is configured to repeat these steps (ii) to (vi) at least y times, where y is greater than 2, until the patient indicates that the lowest stimulus intensity has been seen. Once completed, the processor is configured, by code executing therein, to calculate a visual field score if a percentage of responses in step (vii) labeled as correct is greater than or equal to the percentage expected to be correct based on a historical value for the patient's retinal sensitivity score or an estimated percentage of correct choices based on a probability score.

In one or more particular implementations, the processor is configured to access a historical database of patient data in order to make the comparisons provided in the foregoing steps.

Figure 2:
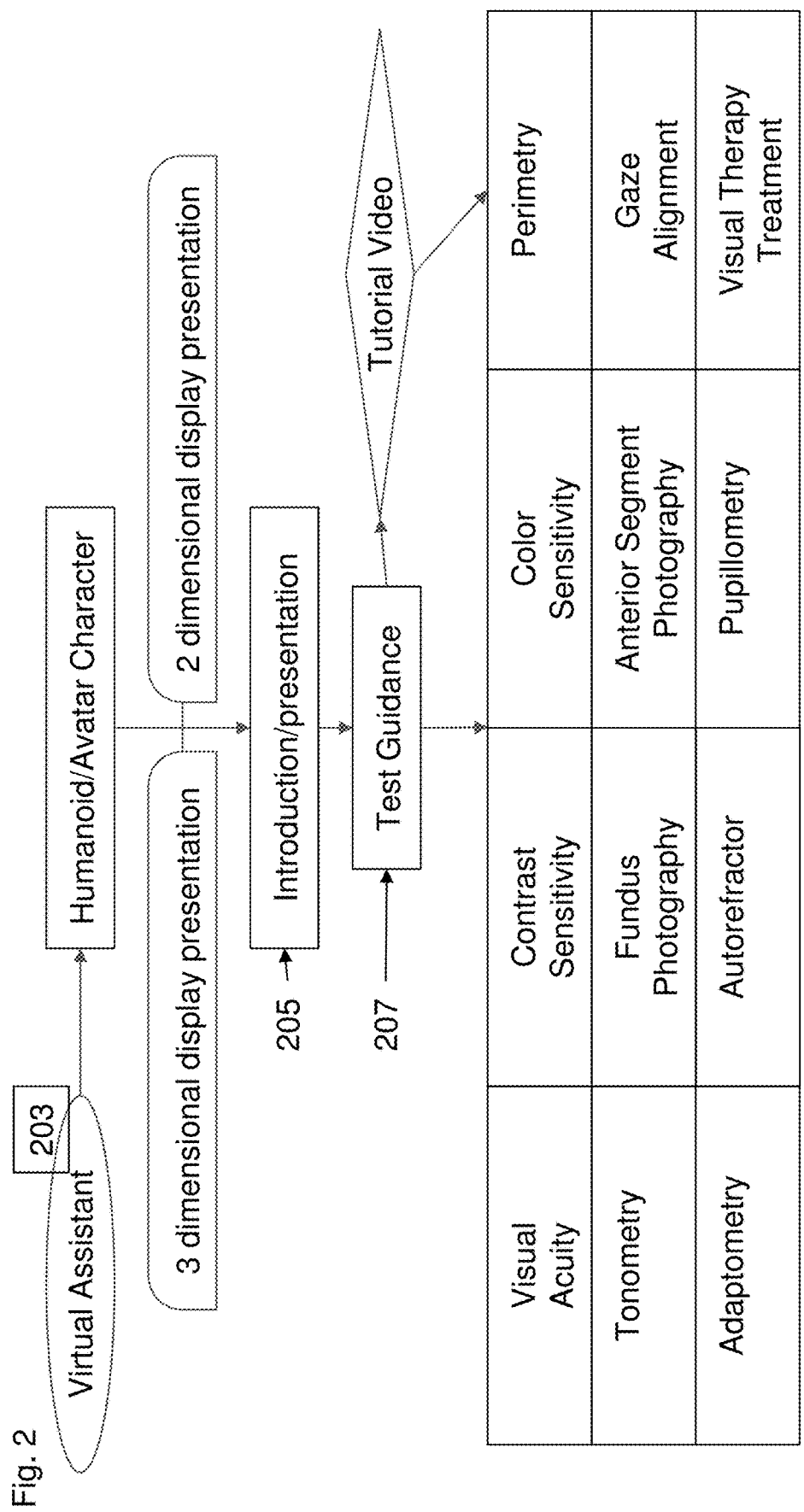
FIG. 2 presents a flow diagram illustrating certain functionality of a system for implementing visual field and other eye tests according to one embodiment of the present invention.

Turning to the flow diagram of FIG. 2, in an alternative workflow of an implementation of the described systems and methods to assist patients to self-perform visual field tests and other ophthalmological tests are provided. As shown, the one or more virtual assistant modules executing as code in a processor of the analysis system 105 configures a processor generate a virtual assistant 203. As described, the user testing platform 103 includes a head mounted or other display device that uses one or more display elements to project a scene into the field of view of the user. In one particular implementation, the display device of the user testing platform 103 incorporates at least a liquid crystal display or an organic light emitted diode display, or any other form of display to present visual guides to patients during ophthalmological self-examinations. The virtual assistant 203 is displayed or otherwise projected into the field of view presented to the user by the user testing platform 103. While the foregoing description refers to a virtual reality-based user testing platform, those possessing an ordinary level of skill in the requisite art will appreciate that the user testing platform 103 can be implemented as a smartphone, computers and internet of things (IoT) so long as such devices are able to provide the functionality as described herein. As shown in FIG. 2, the virtual assistant 203, in accordance with one particular aspect of the concepts described herein, is displayed as an avatar (a humanoid or human-like character) to simulate the presence of a technician, a doctor or any other kind of operator. Such an avatar is presented to provide users with visual guidance on how to self-perform various ophthalmological tests.

As shown in the flow diagram of FIG. 2, the analysis platform 105 is configured to generate a virtual assistant 203 that can interact with the user. It will be appreciated that in certain configurations, the avatar is depicted on both independent screens 1505 and 1507 or two portions of the same screen 1509. In one non-limiting implementation, the virtual assistant 203 is configured to provide audible instructions to a user of the user testing platform 103. In one or more further implementations the virtual assistant 203 is depicted visually. For example, the virtual assistant 203 is depicted as a human or human like character. In one or more further arrangements, the virtual assistant 203 is generated as a 3-dimensional representation of a pre-selected avatar. This 3-dimensional representation is provided to the user testing platform 103 for display to the user in a manner configured to simulate the presence of the virtual assistant within field of view provided to the user. In another implementation, depending on the capability of the user testing platform 103, the virtual assistant 203 can be provided as a 2-dimensional representation. For example, whether the user testing platform 103 lacks the requisite processing capacity to render a 3-dimensional virtual assistant 203, a 2-dimensioanl representation is provided. However, in certain implementation, the user is able to select the type of display representation of the virtual assistant 203.

Continuing with the flow diagram of FIG. 2, the virtual assistant 203 generated by the analysis platform 105 is configured to access from one or more data storage devices a pre-set selection of visual tests. In one arrangement, the visual test data set includes data values (such as text data) that provides an introduction or presentation regarding the particular test or suite of tests to be conducted, as shown in step 205 of FIG. 2. In a further implementation, the virtual assistant 203 provides guidance to the user or a practitioner to carry out a particular eye test as in step 207. For example, the virtual assistant 203 provides instructions or guidance for the user to self-administer a visual acuity test, a contrast sensitivity tests, a color sensitivity test or a perimetry test. In one or more further configurations, the virtual assistant 203 provides the test guidance in the form of a tutorial or instructional video. For instance, the one or more software modules executed by the analysis platform 105 accesses a local or remote data storage repository where one or more audio, video, audio-visual, text or mixed media data files are stored. These data files are accessible by the analysis platform 105 and transmitted to the user testing platform 103 for display or presentation to the user. For example, the accessed media files provide instructions to the user of the user testing platform 103 how to self-administer a color sensitivity, contrast sensitivity, perimetry or visual acuity test using the user testing platform 103.

Figure 3:
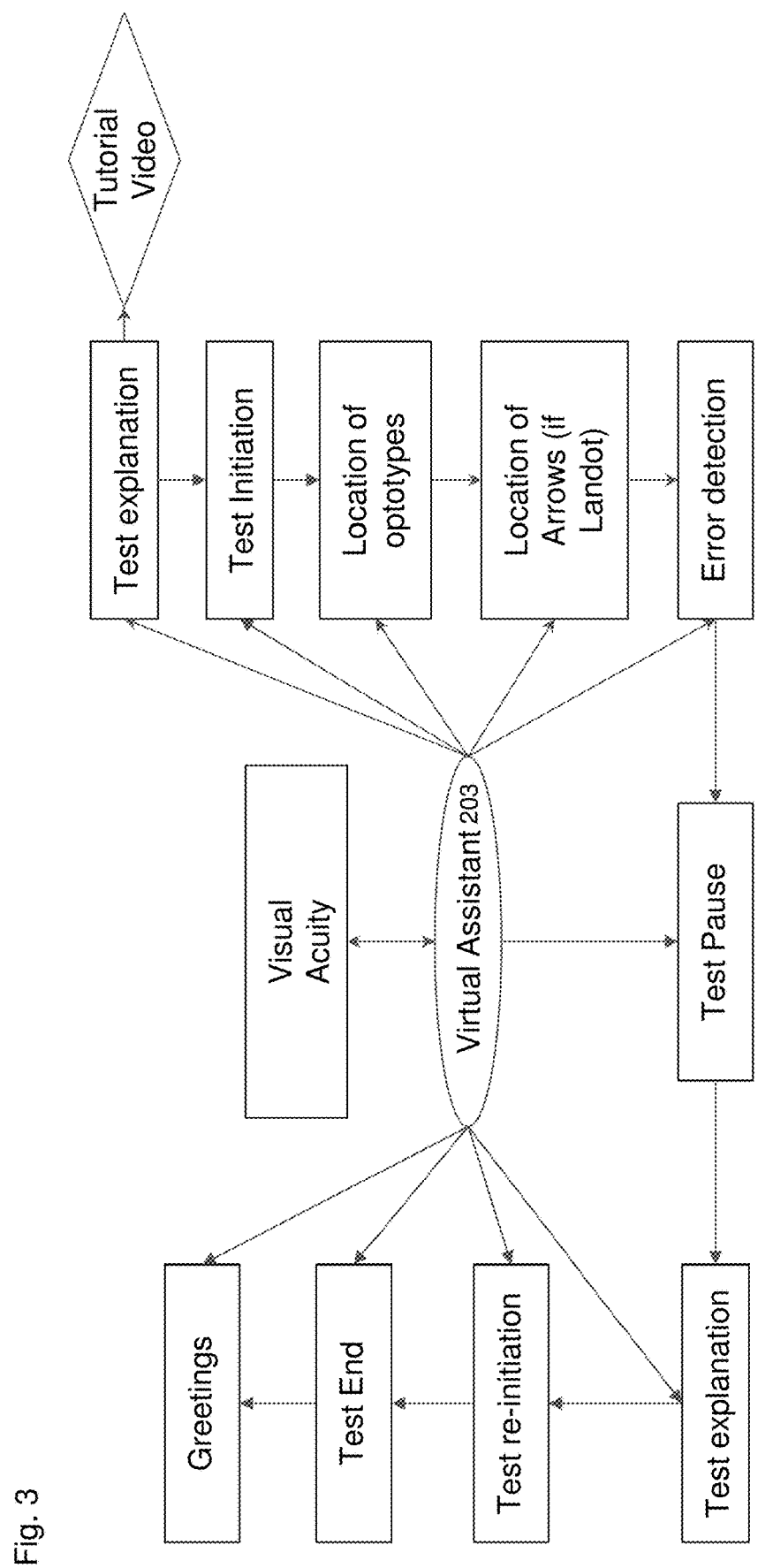
FIG. 3 presents a flow diagram illustrating a software mediated visual acuity test according to one embodiment of the present invention.
Figure 4:
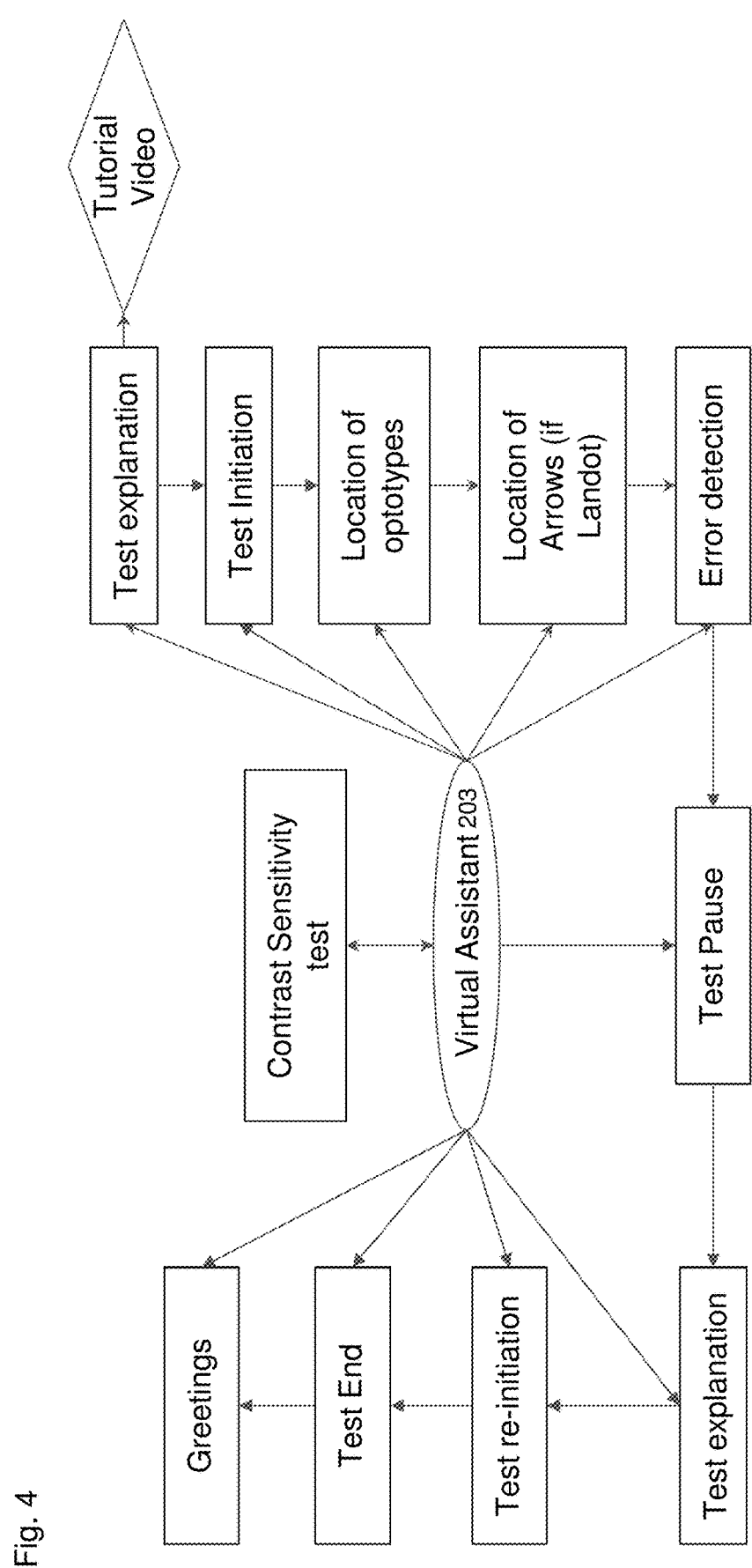
FIG. 4 presents a flow diagram illustrating a software mediated contrast sensitivity test according to one embodiment of the present invention.

Turning now to FIG. 3, a flow diagram is provided that details the virtual assistant mediated testing approach. For example, the virtual assistant 203 provides the to the user a step by step walkthrough on how to carry out several testing tasks associated with a visual acuity test. Here, the virtual assistant 203 is configured to provide displayed visual objects and indicators, such as arrows, written messages, highlighted geometrical figures, flickering areas or any other kind of visual guidance to help patients self-perform ophthalmological tests.

By way of further example, the virtual assistant 203 provided by the analysis platform 105 is configured to access one or more instruction modules that provide the user with steps to carry out a specific visual test. As shown in the non-limiting example of FIG. 3, the virtual assistant 203 is configured to provide a test explanation, a test initiation, location of optotypes, locations of arrows (in the test is a Landolt test). The virtual assistant 203 is further able to determine if an error in the self-administered test has occurred. For instance, when such an error is detected, such as by analyzing the response from one or more sensors integrated into the user testing platform 103 (such as one or more eye tracking sensors), the progress of the self-administered test is paused. Here, the virtual assistant 203 can provide the user with an explanation of the error and how to correct or prevent such an error from occurring. From this step, the virtual assistant 203 continues to monitor the re-initiated test until successful completion and presentation of the results.

Figure 5:
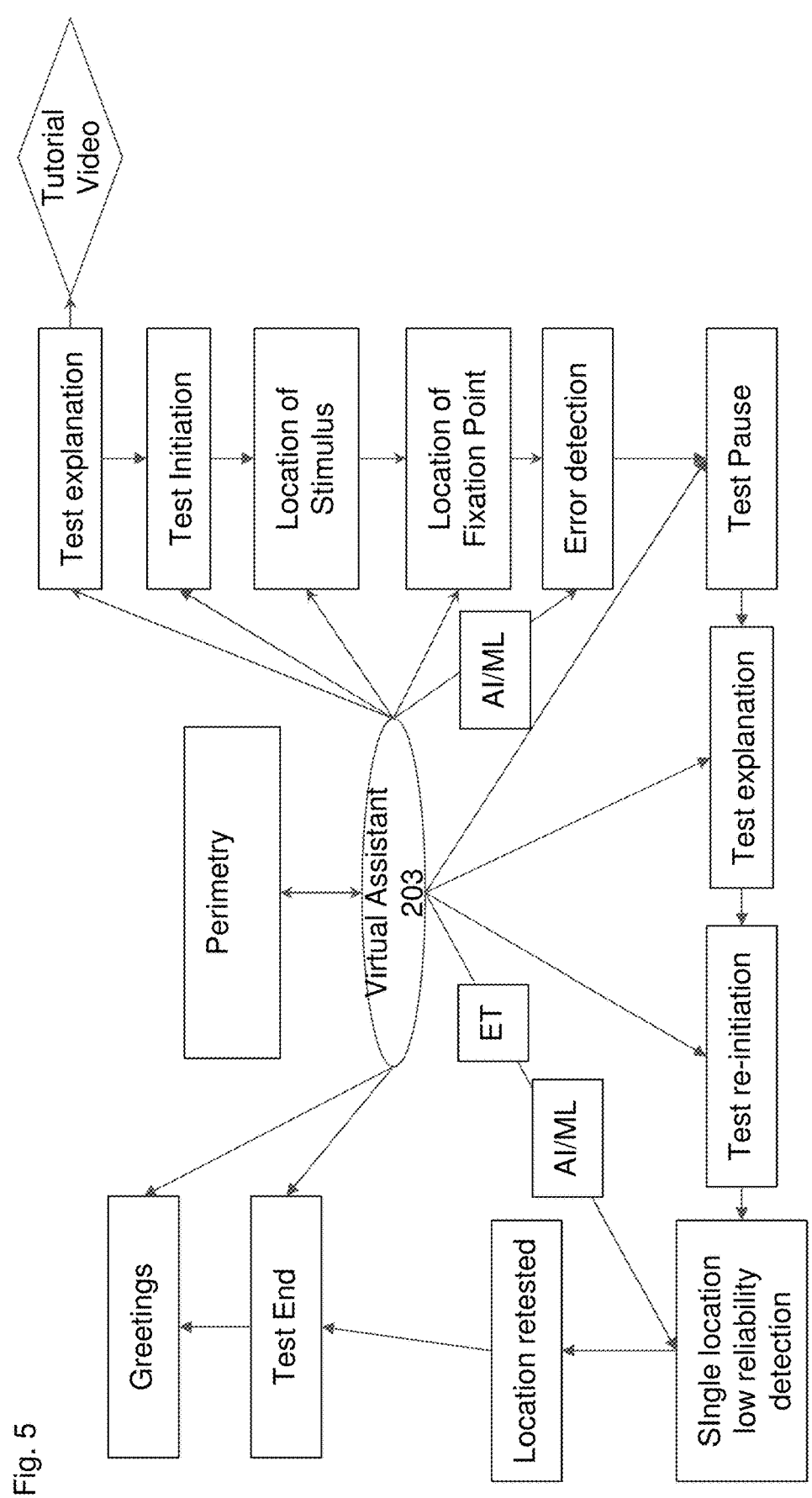
FIG. 5 presents a flow diagram illustrating a software mediated visual field test according to one embodiment of the present invention.
Figure 13:
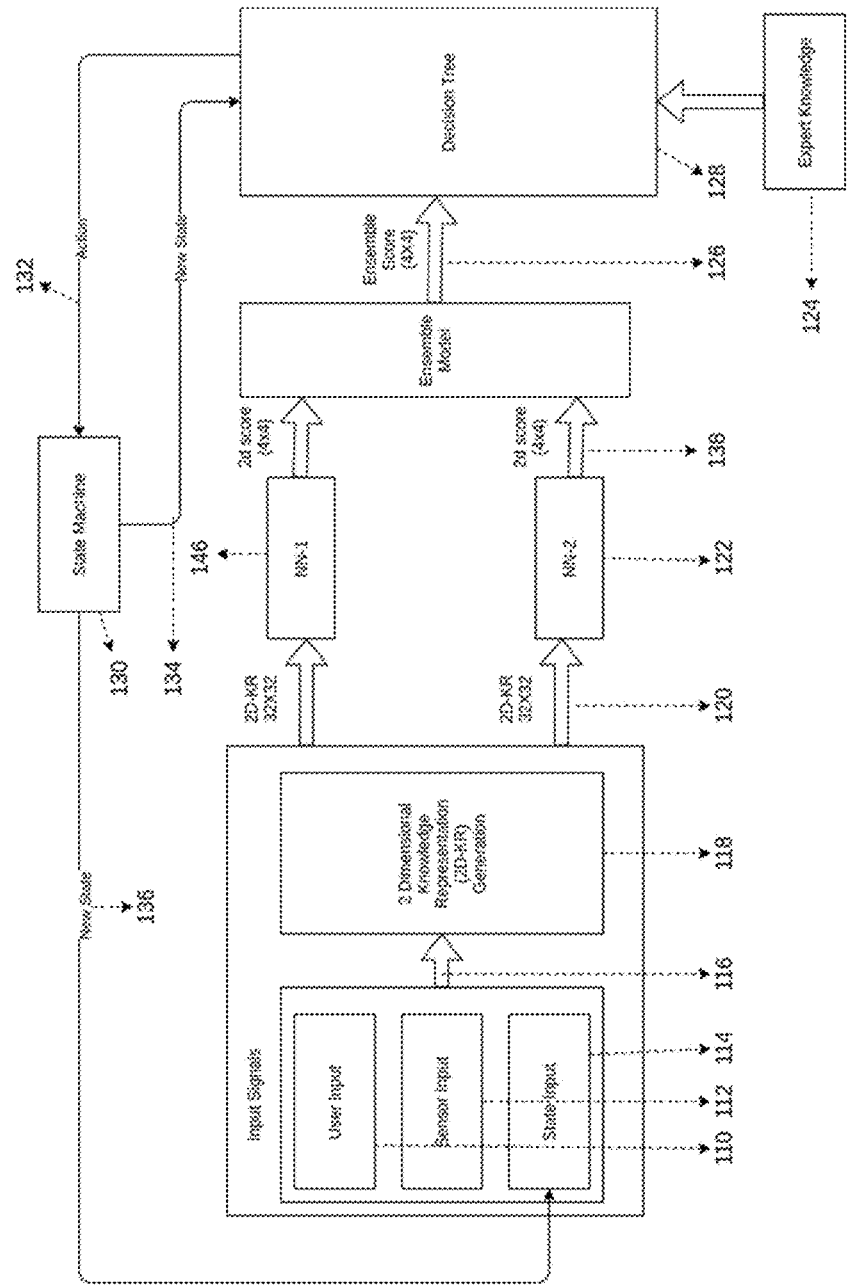
FIG. 13 presents a component diagram illustrating certain details of the predictive system 109 (of FIG. 1)

With respect to the artificial intelligence or machine learning functionality provided in FIG. 5, such artificial intelligence systems can be implemented as a separate predictive system 109 (of FIG. 1), and as further detailed in FIG. 13. In one particular implementation, the configuration detailed in FIG. 13 provides data and predictive models to the analysis platform 105. In turn, the data and predictive models are used to generate changes to the display presented to a user in connection with the tasks being performed.

In one or more particular implementations of the systems and methods described herein, a predictive system (such as the system detailed in FIG. 13) includes two (2) neural networks, a first neural network 122 and a second neural network 146. In alternative configuration additional neural networks, such as three (3) or more neural networks can be used. Each neural network can be trained using a training database 111.

In one particular implementation, the training database 111 includes two-dimensional knowledge representation (2D-KR) 140 of all input signals including user input, sensor input, the state input of the system and labels. In one particular implementation the state input of the system corresponds to the current state of the system, such as whether the system is currently administering a test, and if so, what portion of the test is currently being administered.

Figure 14:
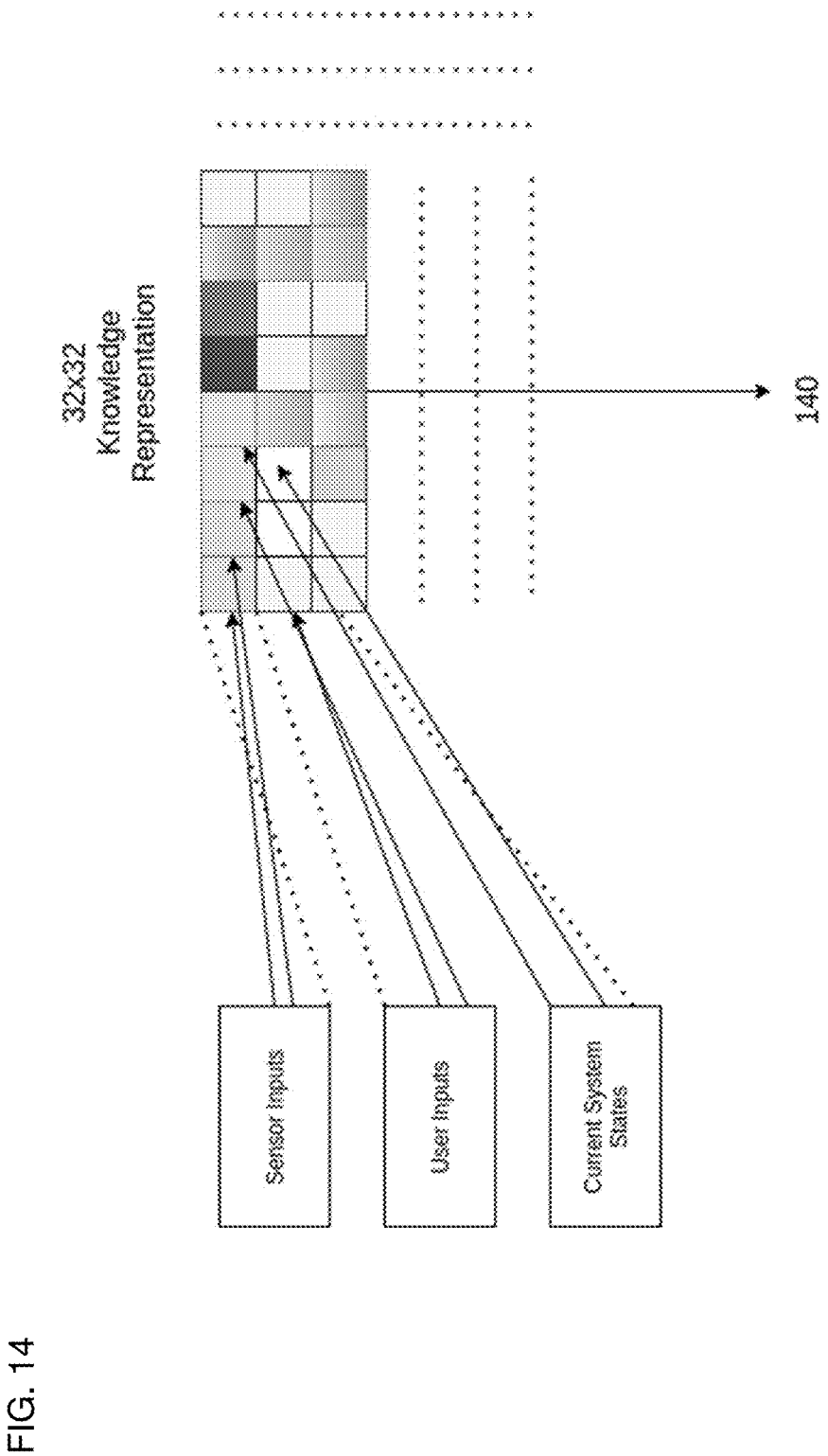
FIG. 14 presents a component diagram illustrating one particular implementation of the two-dimensional knowledge representation (2D-KR)

In one arrangement, the 2D-KR representation of the input data is provided in the form of a 32×32 array, with each cell or array element having a numeric value representing an input value as shown in FIG. 14. In a further implementation, the labels include one or more flags to indicate or identify whether the test encountered significant errors or was unreliable or any other meaningful outcome. For example, where the test encountered an error (such as the number of incorrect answers given by the patient was above a pre-determined threshold), a flag can be applied to the label that categorizes the particular element.

In the foregoing example, both the first and second neural networks 122, 146 can be convolutional neural network (CNN) based deep neural networks.

In one or more implementations, the first neural network 122 can be selected as a very deep neural network (e.g., ResNext-152) and the second neural network 146 can be selected as a relatively fast learning model with a smaller number of layers (e.g., EfficientNet-B1). Those possessing an ordinary level of skill in the requisite art will appreciate that using two different neural network architectures allows the system to obtain and use both "shallow" information from the data and also deep relationships data. The output of the different neural networks can be combined and also function as an ensemble model. Thus, when used herein, the term model or algorithm can refer to either the output of a single neural network, or an ensemble model of a plurality of neural networks.

Figure 15:
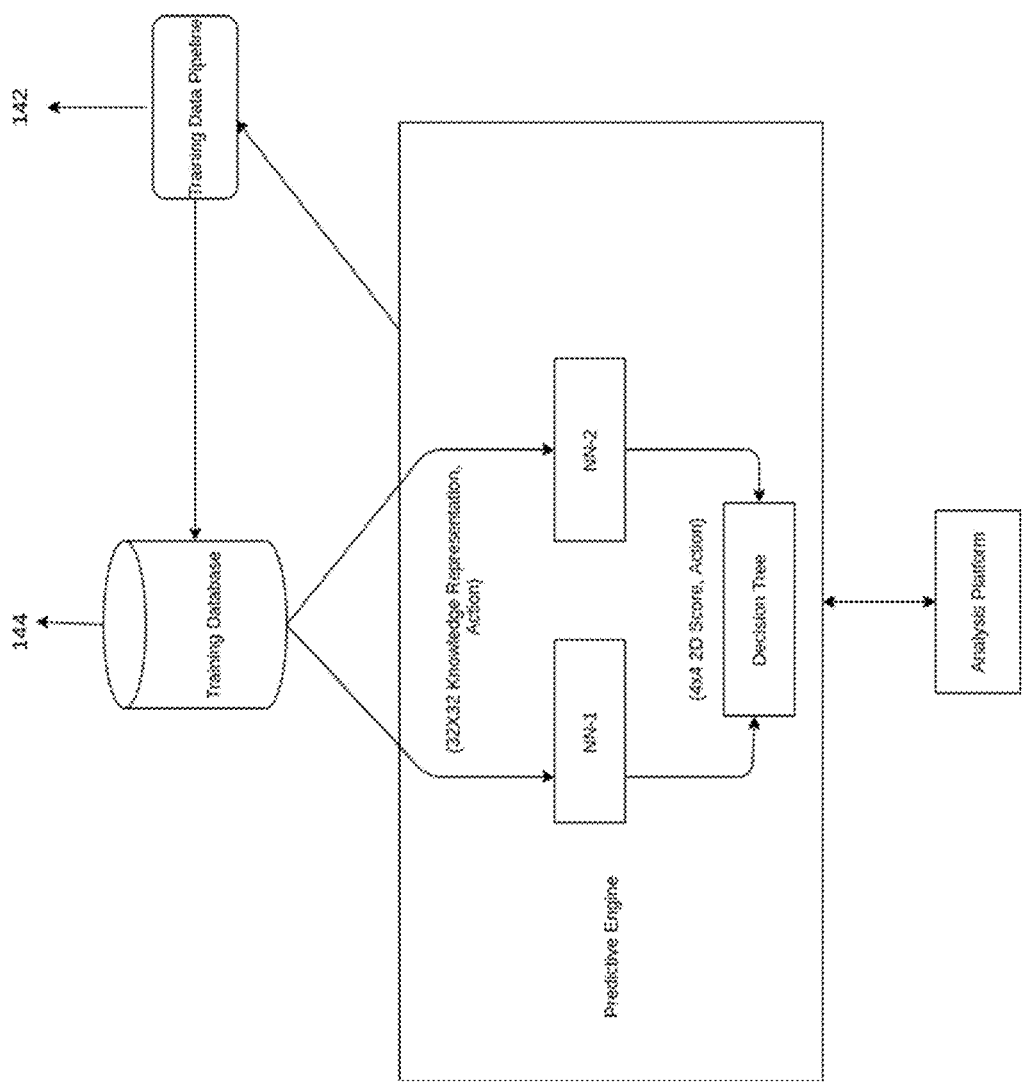
FIG. 15 presents a component diagram illustrating the training phase for the machine learning models.

In a particular implementation a decision tree 128 is integrated into the first and second neural networks 122, 146 during the training phase. In one or more implementations, the decision tree 128 is configured as code executing within a processor of the system. For example, the decision tree 128 is implemented as one or more algorithms that produce a particular output based on supplied input values. As shown in FIG. 15, the decision tree accepts the output of the plurality of neural networks generated from data from the training database. In the illustrated configuration, the provided training phase does not include the ensemble model. However, it should be appreciated that in alternative implementations the ensemble model is used in the training phase.

In one implementation of the training configuration, the neural networks 122, 146 outputs can be directly fed into the decision tree 128. Here, the training flow is further detailed in relationship to FIG. 15 and described herein. After a test completion, data relating thereto is obtained and stored for further use. Specifically, for each step during the testing process, the 2D-KR for each decision-making process during the test; the actions taken for each 2D-KR input; and the state of the system are be recorded and sent to the Training Data Pipeline 142.

In one particular implementation, the training data pipeline 142 can asynchronously or synchronously process the incoming features and labels and store it in the training database 111 for offline training.

During the offline training, there can be two separate training sets for each neural network 122, 146. For each neural network 122, 146; the training starts with the data from the training database 111 being provided to the input layer of the neural network. After the data is processed by the neural network layers and output from an output layer, the processed data is provided to the decision tree 128. Based on the action decided by the decision tree 128; a loss value is calculated and back-propagated to the models to update the weights within the model. In the foregoing description, it will be understood that back-propagation refers to the adjustment of weight values within the layers of a neural network so that the input value is transformed into a target output value.

During the execution, in a preferred embodiment, a predictive system 109 receives sensor data 112 such as data originating with sensors 901, user input 110 and the state input 136. An example state input can be a numeric identifier or list of numerical identifiers that represents the current state of the system which may include but not limited to the followings; the step in the training flow, the time of day, time elapsed since the test started, the test being taken or user information.

Once a predictive system receives the inputs; it can generate a representation of such data, such as the two-dimensional representation (2D-KR) 118 as shown in FIG. 13.

In one or more of the foregoing implementations, the predictive system can use inputs obtained during the examination or test. By way of non-limiting example, the following inputs can include data or values corresponding to the current test step; the battery level of the headset, or other hardware device; the current duration of the test; one or more values corresponding to excessive amount of false positive responses; one or more values corresponding to an excessive amount of false negative responses; one or more values corresponding to a given amount of time without the system detecting a response from the patient; one or more values corresponding to a given amount of time without the system detecting a handpiece movement; one or more values corresponding to a given position of the headset; one or more values corresponding to a detection of a user or patient eye state (such as eyes closed) by the eye-tracking system (ETS) during a given amount of time; one or more values corresponding to an excessive amount of fixation losses; one or more values corresponding to a non-expected number of incorrect responses are detected; one or more values corresponding to an excessive amount of incorrect arrows detection; one or more values corresponding to an incorrect selection of arrows; one or more values corresponding to an incorrect eye position; one or more values corresponding to a given position of the headset and/or the camera device.

In each of the foregoing examples, the term "incorrect" or "excessive" can be established by way of a pre-set threshold value for the given data feature. For example, the value for excessive amount of incorrect arrow detection can be established through one or more statistical analysis on the anticipated amount of incorrect arrow detections. Similar statical values or pre-determined thresholds are known, understood and appreciated by those possessing an ordinary level of skill in the requisite art.

Turning back to FIG. 13, the generated data values provided as part of the knowledge representation (as shown in elements 120, 140) are then input to the CNN based trained neural networks 122, 146 for further evaluations and processing.

The outputs of the neural networks 122, 146, are in one implementation, used to generate an ensemble two-dimensional score 126 of the input data obtained.

The generated ensemble scope 126 is, in one implementation, provided as an input to a decision tree 128. Here, the decision tree is configured by code or algorithm to generate a value that corresponds to the next action to be taken by the visual assistant.

The decision tree 128 can be a categorical variable decision tree which is prepared using expert knowledge source 124. A categorical variable decision tree includes categorical target variables that are divided into categories. For example, the categories can be the actions that the virtual assistant can take at any moment. The categories mean that every stage of the decision process falls into one of the categories. Furthermore, in one or more implementations the decision tree lacks any in-between or intermediate steps between categories.

The output of the decision tree 128 can be an, signal, flag, code, values, function or instruction that the virtual assistant is configured to receive and implement. Once the corresponding action is taken by the virtual assistant, the state machine 130 will change the state of the virtual assistant and feed the new state as an input signal to the decision tree 128 (as shown in 134). In a further implementation, shown in FIG. 13, the new state (as shown in 136) can be provided to the predictive engine for further processing according to the process described herein.

In one or more implementations, the predictive system described herein is configured to take one or more actions in response to the output of the decision tree. Thus, in a particular implementation, the predictive system configures the virtual assistant to revise or alter information dynamically in response to the user's own actions. Here, the responses can be text, audio or visual data that is accessed from a database of pre-set responses. Alternatively, the responses can be dynamically generated based, in part on the current state values.

By way of non-limiting example, the followings are some examples of what the actions the predictive system can undertake:

In one implementation, the virtual assistant accesses and provides to the user one or more stored responses that explains how to avoid responding more than the expected number of responses.

In one implementation, the virtual assistant accesses and provides to the user one or more stored responses that explain what a stimulus is and how to respond when said stimulus is presented.

In one implementation, the virtual assistant accesses and provides to the user one or more stored responses that interrupts the test process in order to explain where to look at (fixation) during the test and the importance of keeping said fixation.

In one implementation, the virtual assistant accesses and provides to the user one or more stored responses that explains what an arrow is, its position and how to select it.

In one implementation, the virtual assistant accesses and provides to the user one or more stored responses that explains what an optotype is and how to respond when said optotype is presented.

In one implementation, the virtual assistant accesses and provides to the user one or more stored responses that explains how to follow the fixation target to all given positions.

In one implementation, the virtual assistant accesses and provides to the user one or more stored responses when the virtual assistant identifies when the patient is falling asleep and intervenes to avoid patient falling asleep during the test.

In one implementation, the virtual assistant accesses and provides to the user one or more stored responses to provide the user with positive reinforcement of good behavior when the patient is correctly following instructions.

In one implementation, the virtual assistant accesses and provides to the user one or more stored responses configured to reduce patient anxiety during the training and testing experience by using strategies such as but not limited to providing positive feedback, pausing the test to provide a break, playing musical background and giving the estimated time remaining to complete the test.

By way of further overview of neural networks, when a network is generated or initialized, the weights are randomly set to values near zero. At the start of the ANN training process, as would be expected, the untrained ANN does not perform the desired mapping of an input value to a target value very well. A training algorithm incorporating some optimization technique must be applied to change the weights to provide an accurate mapping. The training is done in an iterative manner as prescribed by the training algorithm. The optimization techniques fall into one of two categories: stochastic or deterministic.

Training data selection is generally a nontrivial task. An ANN is only as representative of the functional mapping as the data used to train it. Any features or characteristics of the mapping not included (or hinted at) within the training data will not be represented in the ANN.

In one non-limiting example, one or more neural networks are used to generate a model that evaluates sensor or user input data and outputs a status flag or signal. For instance, the neural network could be trained to provide a value indicating the probability that an error in a visual test has occurred based on the sensor values measured during the testing phase. In another implementation, an artificial neural network, machine learning algorithm, or other statistical process is used to evaluate sensor or user input data received from the user testing platform 103 and output a predicted score of one or more different forms of visual field tests. In another arrangement, a machine learning or neural network derived model is configured to generate a threshold or cutoff value for evaluating user produced data, where values above the threshold value have a high correlation with a first given outcome and measurements where the values are below the threshold have a correlation with a second given outcome.

Figure 6:
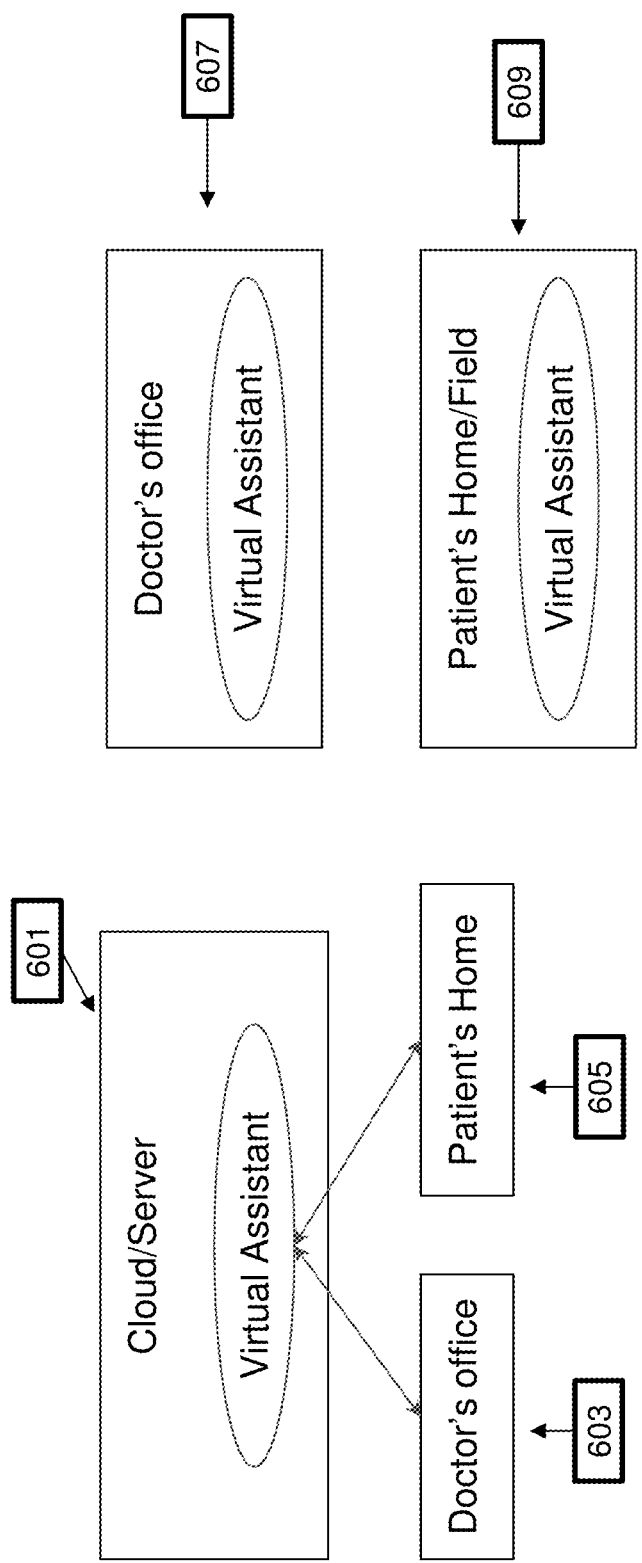
FIG. 6 presents a block diagram illustrating components a software mediated virtual assistant platform according to one embodiment of the present invention.

Turning now to FIG. 6, in one or more of the foregoing implementations, the virtual assistant 203 is generated and operated by an analysis platform 105 that is instantiated or provided by code executing on a server or remote computer 601. Such a server or remote computer 601 can be a cloud or remote computing platform that is configured to exchange data with one or more client computers 107. In one arrangement, the client computers are located at a physicians' office 603 or at the user's preferred location, such as their home or care facility 605. In a particular implementation, the user testing platform 103 directly exchanges data with the server or remote computer 601.

In a further implantation, the client computer 107 is an intermediary processor or platform that is configured to receive data from the cloud or remote system, such as analysis system 105 and provide that data to the user testing platform 103 as modified or altered instructions. For example, where the user testing platform 103 does not have direct access to a computer network, the user testing platform 103 is connected, by wireless or wired connection, to the analytic platform 105 in order to exchange data with the user testing platform 103. In an alternative configuration, the virtual assistant 203 is configured as a local software agent. For instance, the analytic platform 105 is instantiated as a collection of software modules executing on a processor of a local computer 107 or processing platform that is capable of generating a virtual assistant 203 without accessing any remote resources. For example, where a computer of sufficient capability is located on the premises of a doctor's office 607 or a patient's home 609, such local computers directly provide the virtual assistant to the user undergoing vision testing.

Figure 7:
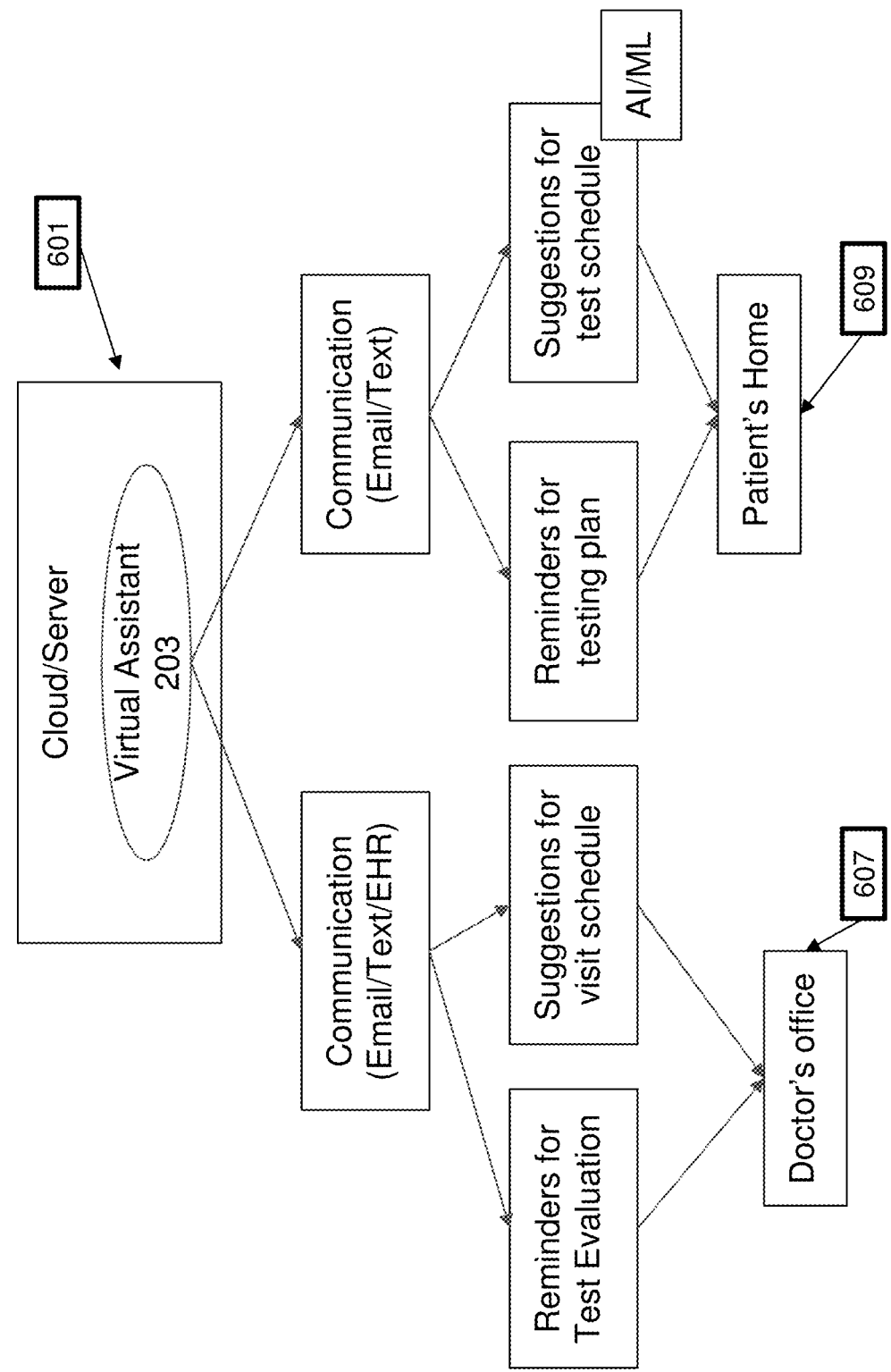
FIG. 7 presents a flow diagram illustrating steps for carrying out reminders to doctors and patients in accordance with one embodiment of the present invention.

As shown in FIG. 7, where the analysis system 105 configured to generate the virtual assistant 203 is remote from the user testing platform 103, such as being implemented as a cloud server 601, the analysis system 105 includes one or more communication modules (such as code executing within one or more of the processors of the cloud server 601) that instruct the analysis system 105 to generate communications or messages for a particular user. These generated messages include one or more customizable messages that are addressed to the user of the user testing platform 103 or to an administrator of tests (such as a physician). The intended recipients of these generated messages can be determined based on one or more pre-set or dynamic rules that have been provided to the analysis system 105. For instance, the analytic system is configured to generate messages for transmission to a user to provide reminders or suggestions regarding testing plans or schedules for administering a visual test or an analysis of the user's visual status. In one particular implementation, the analysis platform 105 incorporates one or more further analytic or predictive models or modules (such as one accessed or received from the predictive engine 109) that configures a processor of the analysis platform 105 to suggest, via the virtual assistant 203, test schedules based on a predictive model. For instance, a predictive model can be generated by the prediction engine 109 that has accessed a training set of data, such as data accessed from training database 111, where such a model is trained to indicate when the highest compliance for a scheduled test occurs. Using this pretrained model, the analysis platform 105 is configured to select a date or time, or a combination thereof, that has a high probability of resulting in test compliance and suggest this date to the user via the virtual assistant 203.

Figure 8:
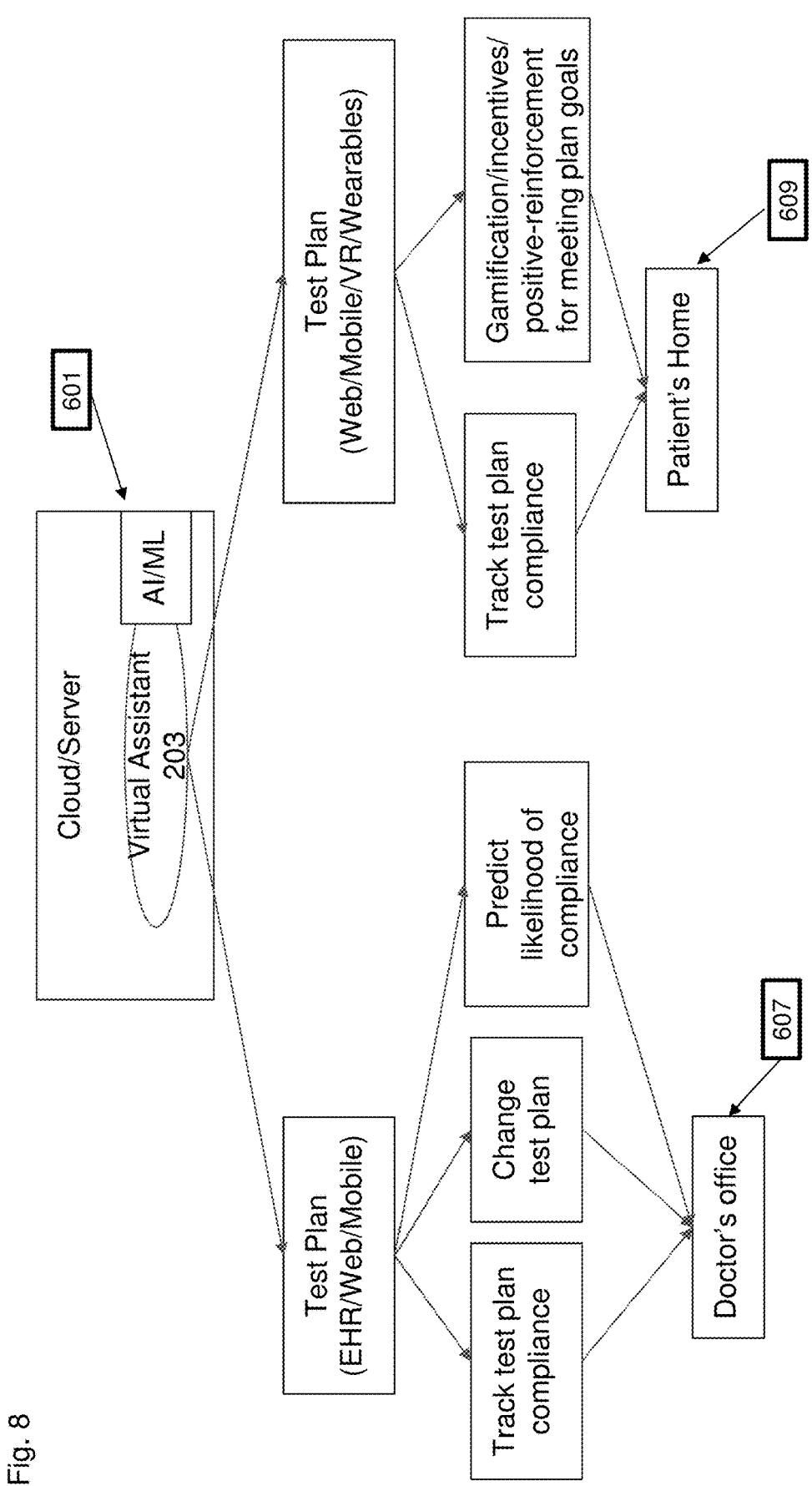
FIG. 8 presents flow diagram illustrating steps for carrying out communication with electronic medical records and evaluating compliance in accordance with one embodiment of the present invention.

Turning now to the flow diagram of FIG. 8, the analysis platform 105 is configured with one or more analytic or predictive models (again, in one implementation obtained from the predictive engine 109) to provide data to be used by the virtual assistant 203. For example, using predictive algorithms, the virtual assistant 203 is configured by the analysis platform 105 to provide a testing plan to a user or to a user's physician. For instance, the analysis platform 105 utilizing a testing predictive model obtained from predictive engine 109 is configured by one or more modules to evaluate test plan compliance across a given patient population and derive from that evaluation one or more relevant factors or variables that contribute to testing plan compliance. Using these identified variables or factors, the particular data points corresponding to a given patient are evaluated by the analysis platform 105 using a predictive model such that the likelihood that a patient will comply with a given plan is evaluated. Where the analysis platform 105 predicts that the likelihood that the plan will be complied with is below a pre-set threshold value, the analysis platform 105 is configured to adjust one or more parameters of the test plan. For example, the date and/or the time of the test plan are altered dynamically until the likelihood of test compliance exceeds the pre-determined threshold value.

Furthermore, while interfacing directly with the user, a remote analysis platform 105 (such as a server-based engine 601) is configured to also track self-administered test compliance. Where the reviewed data indicates that the user is non-compliant or semi-compliant with a given testing plan, the analysis platform 105 is configured by one or more enhanced engagement modules to provide the user with positive reinforcement or incentives to become or increase their compliance with the testing plan.

As shown in FIG. 9 the user testing platform 103 is configured as a virtual reality or augmented reality device that is configured to provide commands to a user. In one particular arrangement, as further shown, a virtual assistant 203 interfaces or receives data from the user platform 103 such that data from one or more of gyroscopes 912, accelerometers 914, pressure sensors 910, magnetometers 908, orientation tracking units (IMU) 902, structured light scanners 904 and IR-based position tracking sensors 906 to provide feedback and guide patients during ophthalmological self-examinations. In one particular implementation, the data collected by the sensors 901 provided herein are transmitted to the analysis platform 105 for further review and analysis. In response to this review and analysis, the virtual assistant 203 is configured by one or more software modules of the analysis platform 205 to generate or provide instructions to the user in order to administer or self-administer a text or exam.

Figure 10:
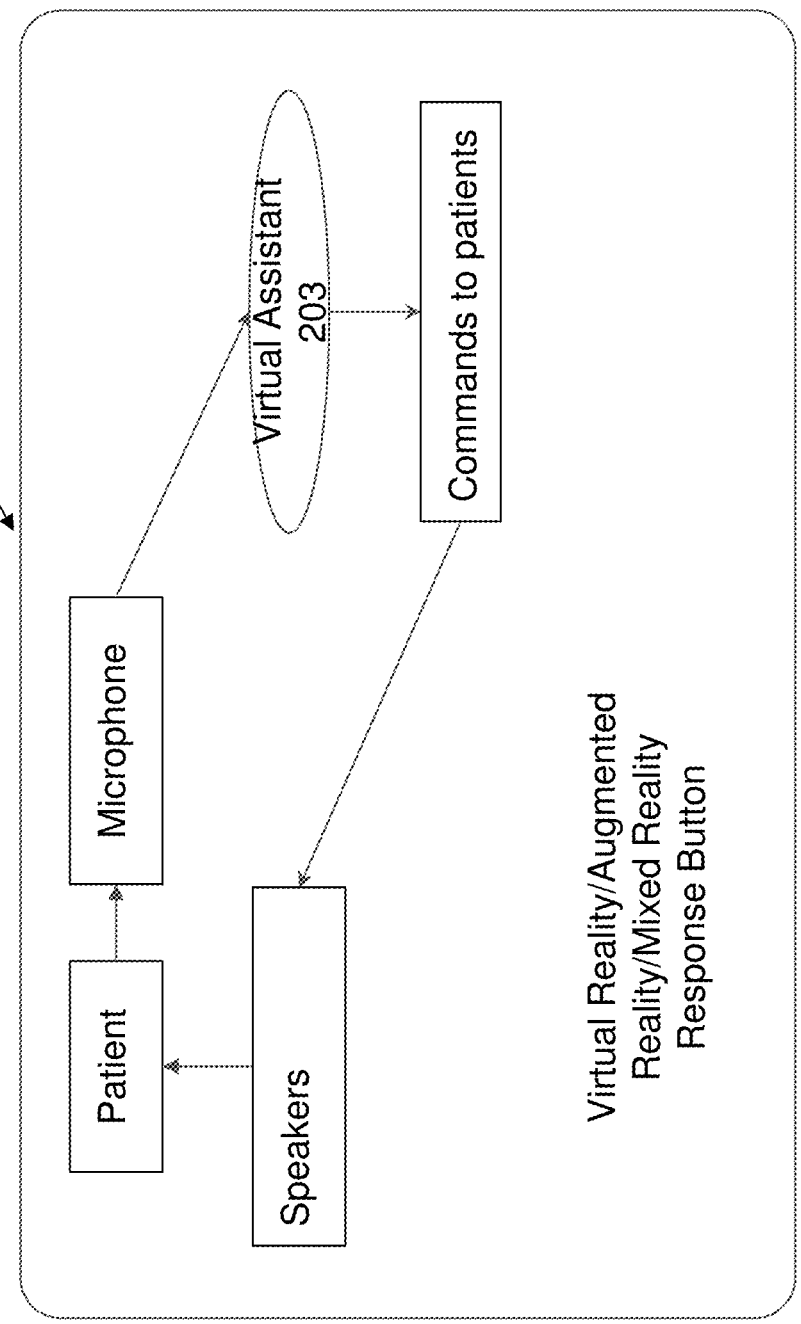
FIG. 10 presents a component diagram of the use of an eye testing device process for executing eye testing verbal instructions in accordance with one embodiment of the present invention.

As shown in FIG. 10, in a particular implementation, the virtual assistant 203 is configured to receive data generated by the user during operation of the user testing platform 103. For instance, the analysis platform 105 is configured to receive audio data from a microphone incorporated or associated with the user testing platform 103. By way of non-limiting example, the virtual assistant 203 implemented by the analysis platform 205 accesses the microphone data and speaker systems of the user testing platform 103 to receive audio data and transmit information with the user. For example, the virtual assistant 203 is enabled to parse and evaluate speech provided by the user and respond by synthesizing sounds to provide verbal guidance on how to self-perform ophthalmological tests. By way of further example, the virtual assistant 203 uses microphone to collect voice/commands from the patient using the user testing platform 103. A virtual assistant 203 is configured by the analysis platform to send the audio data to the analysis platform 105 for parsing, natural language processing and evaluation. Once processed, the appropriate responses to the user's input (such as a response to a user question) are transmitted back to the user testing platform for output via the speakers or headphones. Such a response can be configured to provide a patient with guidance on how to self-administer any kind of therapies, such as but not limited to, photo-biomodulation.

Figure 11:
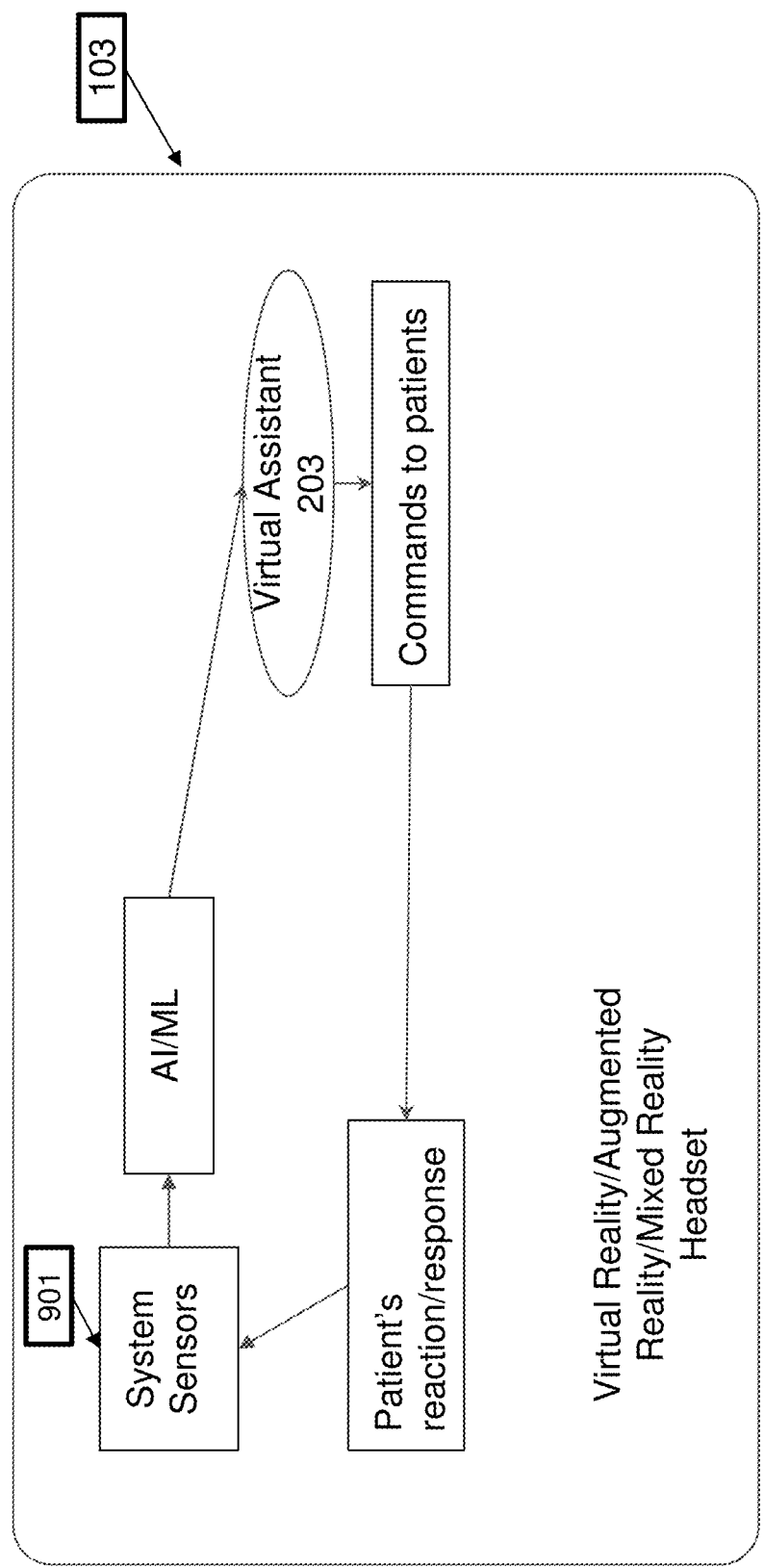
FIG. 11 presents a component diagram illustrating a process for executing a eye testing instructions on a patient in accordance with one embodiment of the present invention.

As shown in FIG. 11, a virtual assistant 203 is configured to use any kind of artificial intelligence, machine learning or statistical methodology to evaluate data obtained from the sensors 901. For example, the predictive engine 109 utilizes one or more models generated by a convolutional neural network, support vector machine, linear regression, Bayesian analysis, trait modeling, or other analysis techniques known and understood in the art to simulate a technician, a doctor or any other kind of operators of the user testing platform 103. For example, the virtual assistant 203 utilizes a predictive model to provide users with audiovisual guidance on how to self-administer psychophysical tests.

It will be appreciated that in the embodiment depicted in FIG. 11, the predictive models are local to the user testing platform 103. A virtual assistant that is also local to the user testing platform 103 uses these predictive models to determine the most efficient and accurate algorithm for presenting any kind of stimulus during any psychophysical self-test. In a further implementation, the virtual assistant approach described herein uses one or more different analytical or predictive models to determine the degree of patient's understanding of a given test. Using such information, the virtual assistant can skip certain instructions and otherwise avoid spending the user's time on education about the psychophysical testing procedures.

Figure 12:
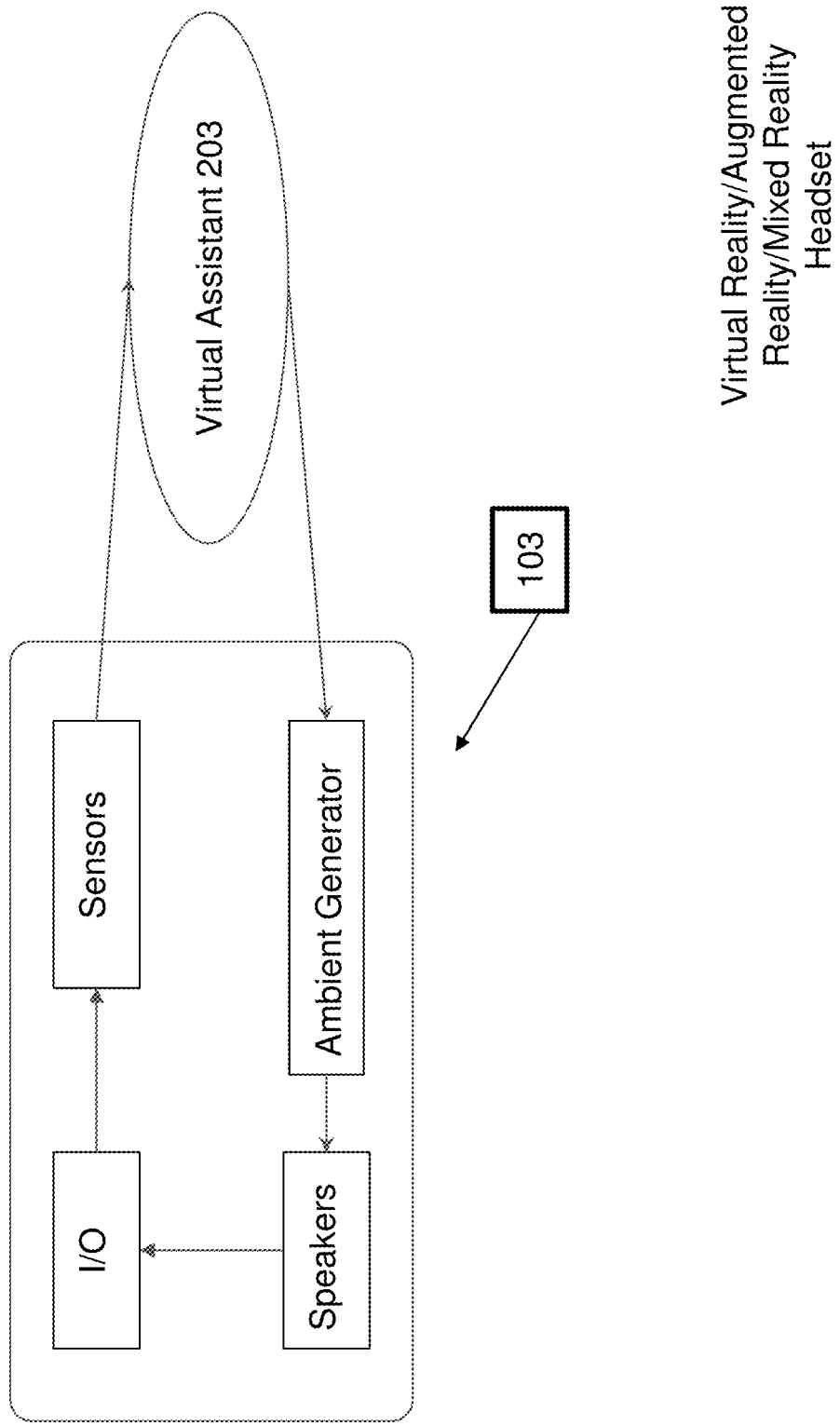
FIG. 12 presents a component diagram illustrating a process for executing a eye testing instructions on a patient in accordance with one embodiment of the present invention.

As shown in FIG. 12, a virtual assistant 203 is provided that recreates a peaceful environment to make the patients feel comfortable and relaxed before, during and or after ophthalmological tests. Such a peaceful environment can be generated by referencing prior information about the patient, or a statistical model or predictive system that takes into account user sensor data obtained from the user testing platform 103. Such prior data can be used to determine one or more appropriate environmental changes that have a high likelihood of reducing the user's present anxiety or agitation. For example, the virtual assistant 203 is configured to provide conversational topics to the user that will reduce stress and anxiety. In another non-limiting implementation, the virtual assistant 203 provides music or a change in the tone, or color of the background of the virtual reality environment to a more relaxing color palate.

In one or more particular implementations, the virtual assistant 203 is configured by the neural network generated models to dynamically and automatically adjust the testing process so as to direct the user. For example, the virtual assistant described herein is configured by one or more modules, configured as code executed by a processor, to evaluate user input and dynamically change the content displayed or provided to the user in response to an evaluate of the current state of the user as determined by the user input and sensors.

For example, the following are non-limiting examples of test action taken or implemented by the virtual assistant based on AI algorithm decision or classification. For example, in one non-limiting implementation, a system is provided, wherein the virtual assistant uses neural network (NN) or a support vector machine (SVM) to classify several patient's input to the system and provide a subsequent test action.

By way of further example, a system is provided where a processor is configured by an algorithm to trigger the intervention of a Virtual Assistant (VA) during a visual field test where it is determined that certain quality criteria are detected. For instance, where the following criteria are detected or determined: excessive amount of false positive responses; excessive amount of false negative responses; a given amount of time without the system detecting a response from the patient; a given amount of time without the system detecting a handpiece movement; a given position of the headset; detection of eyes closed by the eye-tracking system (ETS) during a given amount of time; excessive amount of fixation loses.

In response to a determination that one or more of these criteria have been met, the processor configures the display to generate the virtual assistant such that the visual representation of the virtual assistant can provide prompts and guidance to the user during administration of the visual field test. For example, the processor configures the virtual assistant to be displayed within the visual field of the users. For example, the processor is configured by one or more intervention modules to cause the VA to be provided as an overlay of the existing content provided by the display device) intervene to provide personalized explanation of the test based on said quality criteria: the VA explains how to avoid responding more than the expected amount of responses; the VA explains what a stimulus is and how to respond when said stimulus is presented; the VA intervene to avoid patient falling asleep during the test; the VA intervene to explain where to look at (fixation) during the test and the importance of keeping said fixation.

In an alternative arrangement, a system is provided where a processor is configured by an algorithm to trigger the intervention of the Virtual Assistant (VA) in an on-going visual acuity test where one or more intervention criteria are detected. For instance, if certain visual acuity test quality criteria, such as, but not limited to: non-expected amount of incorrect responses are detected; excessive amounts of incorrect arrows detection; incorrect selection of arrows; a given amount of time without the system detecting a response from the patient; a given amount of time without the system detecting a handpiece movement; a given position of the headset; and detection of eyes closed by the eye-tracking system (ETS) during a given amount of time, the virtual assistant is directed to intervene in the testing process and provide prompts or guidance. For example, one or more modules configured as code executed by a processor causes one or more processors to provide personalized explanation of the test based on said quality criteria. For example, the processor is configured to cause the Virtual Assistant to instruct the user to avoid responding more than the expected amount of responses. By way of further example, the VA is configured by one or more modules to access prompts that explain what an arrow is, its position and how to select it. By way of further example, the VA is configured by one or more modules to access prompts or stored text that describe what an optotype is and how to respond when said optotype is presented.

In one or more further implementations, the VA is configured by one or more modules that cause the VA intervene when one or more sensors detect that the patient is falling asleep during the test.

By way of further example, the system is configured by one or more modules to trigger the intervention of the Virtual Assistant (VA) if one or more of the following quality criteria of the contrast sensitivity test are detected: non-expected amount of incorrect responses are detected; excessive amount of incorrect arrows detection; incorrect selection of arrows; a given amount of time without the system detecting a response from the patient; a given amount of time without the system detecting a handpiece movement; a given position of the headset; and detection of eyes closed by the eye-tracking system (ETS) during a given amount of time.

In a particular example, the VA is configured by one or more modules to intervene, such as by providing prompts to the patient, to provide personalized explanation of the test based on one or more of the following quality criteria: the VA provides one or more prompts (such as text or voice based prompts obtained from a database of prompts) that explains how to avoid responding more than the expected amount of responses; the VA explains (using one or more stored or dynamically generated prompts) what an arrow is, its position and how to select it; the VA explains what an optotype is and how to respond when said optotype is presented; and the VA intervene to avoid patient falling asleep during the test.

In one or more further implementations, a system is provided herein one or more modules executing as code in a processor causes the intervention of the Virtual Assistant (VA) if certain dark or light adaptometry test quality criteria are detected. For example, the VA can be triggered to interact with the patient where: non-expected amount of incorrect responses are detected; excessive amount of incorrect arrows detection; incorrect selection of arrows; a given amount of time without the system detecting a response from the patient; a given amount of time without the system detecting a handpiece movement; a given position of the headset; and detection of eyes closed by the eye-tracking system (ETS) during a given amount of time.

Here, the system configures to the VA intervene to provide personalized explanation of the test based on said quality criteria. For example, the VA can be configured by one or more intervention modules to: explain (through the use of one or more visual or audio prompts) how to avoid responding more than the expected amount of responses; explain what an arrow is, its position and how to select it; explains what an optotype is and how to respond when said optotype is presented; and intervene to avoid patient falling asleep during the test.

In one or more further implementations, a system is provided herein one or more modules executing as code in a processor causes the intervention of the Virtual Assistant (VA) if certain tonometry test quality criteria are detected. For example, the VA can be triggered to interact with the patient where: the system determines that there is incorrect eye position; the patient is determined to be in a given position, based on the positioning of the headset and/or the camera device; and the eyes of the patient are determined, by the eye-tracking system (ETS), to be closed for a pre-determined amount of time.

Here, the system configures to the VA intervene to provide personalized explanation of the test based on said quality criteria. For example, the VA can be configured by one or more intervention modules to: explain how to follow the fixation target to all given position; and cause the VA to intervene (such as producing an audio or visual alert) to avoid patient falling asleep during the test.

In one or more further implementations, a system is provided herein one or more modules executing as code in a processor causes the intervention of the Virtual Assistant (VA) if certain ophthalmic photography test quality criteria are detected. For example, the VA can be triggered to interact with the patient where: incorrect eye position is detected; a given position of the headset and/or the camera device is detected; and detection of eyes closed by the eye-tracking system (ETS) during a given amount of time.

Here, the system configures to the VA intervene to provide personalized explanation of the test based on said quality criteria. For example, the VA can be configured by one or more intervention modules to: explain how to follow the fixation target to all given position; and to intervene to avoid patient falling asleep during the test.

In one or more further implementations, a system is provided herein one or more modules executing as code in a processor causes the intervention of the Virtual Assistant (VA) if certain gaze position test quality criteria are detected. For example, the VA can be triggered to interact with the patient where: non-expected amount of incorrect responses are detected; excessive amount of incorrect arrows and/or optotypes detection; incorrect selection of arrows and/or optotypes; a given amount of time without the system detecting a response from the patient; a given amount of time without the system detecting a handpiece movement; a given position of the headset; and detection of eyes closed by the eye-tracking system (ETS) during a given amount of time.

Here, the system configures to the VA to intervene to provide a personalized or dynamically generated explanation of the test based on said quality criteria. For example, the VA can be configured by one or more intervention modules to: explain how to avoid responding more than the expected amount of responses; explain what an arrow is, its position and how to select it; explain what an optotype is and how to respond when said optotype is presented; and intervene in order to avoid patient falling asleep during the test.

In one or more further implementations, a system is provided that is configured by one or more modules executing as code in a processor that causes the intervention of the Virtual Assistant (VA) if certain pupillometry test quality criteria are detected. For example, the VA can be triggered to interact with the patient where: incorrect eye position is detected; a given position of the headset and/or the camera device is detected; and detection that the patient's eyes are closed by the eye-tracking system (ETS) during a given amount of time.

Here, the system configures to the VA intervene to provide personalized explanation of the test based on said quality criteria. For example, the VA can be configured by one or more intervention modules to: explain how to follow the fixation target to all given position; and the VA intervene to avoid patient falling asleep during the test.

In one or more further implementations, a system is provided that is configured by one or more modules executing as code in a processor that causes the intervention of the Virtual Assistant (VA) if certain autorefraction test quality criteria are detected. For example, the VA can be triggered to interact with the patient where: incorrect eye position is detected; a given position of the headset and/or the camera device is detected; detection of eyes closed by the eye-tracking system (ETS) during a given amount of time.

Here, the system configures to the VA intervene to provide personalized explanation of the test based on said quality criteria. For example, the VA can be configured by one or more intervention modules to: explain how to follow the fixation target to all given position; and intervene to avoid patient falling asleep during the test.

In one or more further implementations, a system is provided that is configured by one or more modules executing as code in a processor that causes the intervention of the Virtual Assistant (VA) if certain eye and vision therapy quality criteria are detected. For example, the VA can be triggered to interact with the patient where: incorrect eye position is detected; a given position of the headset and/or the camera device is detected; and detection of eyes closed by the eye-tracking system (ETS) during a given amount of time.

Here, the system configures the VA to intervene to provide personalized explanation of the test based on said quality criteria. For example, the VA can be configured by one or more intervention modules to: explain how to follow the fixation target to all given position; and intervene to avoid patient falling asleep during the test.

Additional further implementations of the systems methods and apparatus described herein are understood. For example, and in no way limiting, the following specific, non-limiting numbered implementations are particular configurations of the subject matter described herein.

Implementation 1. A system for a visual acuity test comprising, at least one data processor comprising a virtual reality, an augmented reality or a mixed reality engine and at least one memory storing instruction which is executed by at least one data processor, at least one data processor configured to: present a virtual assistant in virtual reality, augmented reality or mixed reality, wherein the virtual assistant presents to a patient a set of instructions for the visual acuity test, (ii) provide a set of n optotypes, wherein n is greater than or equal to 2, each optotype having a (a) specified size, (b) shape and (c) luminance, wherein the luminance of the optotypes is greater or lower than the luminance of a background; (iii) receive from the patient at least one response when the patient views at least one optotype, wherein the response comprises selection of a position of the at least one optotype or location of an arrow associated with the at least one optotype; (iv) repeat steps (ii) to (iii) at least y times, where y is greater than 2, until the patient indicates that he/she cannot identify any optotypes having a size smaller than the last optotype the patient responded to in step (iii); (v) repeat steps (i) to (iv), wherein the explanation in step (i) is modified based on the patient's response to provide a second set of instructions selected from a library instructions if a percentage of responses in step (iii) labeled as correct is less than the percentage expected to be correct based on a historical value for the patient's visual acuity score or an estimated percentage of correct choices based on a probability score; or (vi) calculate a visual acuity score if a percentage of responses in step (iii) labeled as correct is greater than or equal to the percentage expected to be correct based on a historical value for the patient's visual acuity score or an estimated percentage of correct choices based on a probability score.

2. The system of implementation 1, further comprising a virtual reality, an augmented reality or a mixed reality headset.

3. The system of implementation 1, wherein the set of instructions comprises a patient guide or an explanation of the visual acuity test.

4. The system of implementation 1, wherein the virtual reality comprises augmented reality or mixed reality.

5. The system of implementation 1, wherein the set of instructions in step (i) further comprises noting the location of the optotypes and the location of arrows in the test scenario.

6. The system of implementation 5, wherein the set of instructions further comprises providing information to the patient on timing and sequence of the visual acuity test.

7. The system of implementation 1, wherein the set of instructions further comprises an explanation of responses of the patient.

8. The system of implementation 1, wherein the set of instructions comprises a verbal explanation.

9. The system of implementation 1, wherein the set of instructions comprises a pictorial explanation providing a set of actions and vector movements showing the position of the optotypes. (i) The arrows blink and move indicating to the position of the optotype.

(ii) The optotypes change their appearance by blinking, glowing, changing the color, hue or intensity to attract the attention of the patient being tested.

10. The system of implementation 1, wherein the virtual assistant is humanoid in appearance.

11. The system of implementation 1, wherein the virtual assistant is an avatar.

12. The system of implementation 1, wherein the virtual assistant is a cartoon character.

13. The system of implementation 1, wherein the virtual assistant is presented in two dimensions.

14. The system of implementation 1, wherein the virtual assistant is presented in three dimensions.

15. The system of implementation 1, wherein the virtual assistant is representational.

16. The system of implementation 1, wherein the optotypes are selected from the group consisting of Sloan letters, Snellen E's, Landolt C's, ETDRS optotypes and Lea symbols or combinations of Lea symbols and letters for the pediatric population.

17. The system of implementation 1, wherein the virtual assistant uses neural networks (NN) and a decision tree to evaluate the inputs from patient, sensors and system state and provide a subsequent action.

18. The system of implementation 17, wherein neural networks and a decision tree are previously trained by:

(i) a training database, wherein the training database includes, for each member of a training population comprised of visual acuity tests taken by users, an assessment dataset that includes at least data relating to a respective user response to the visual acuity set and or a sensor input and or a system state.

(ii) a visual acuity score of the respective test; a training system including an expert system module configured to determine correlations between the respective user responses, sensor inputs and system state to the visual acuity test and the visual acuity score of each member of the training population.

(iii) a user testing platform configured to provide a user with a current visual acuity test and receive user input regarding responses to the current visual acuity test; an analysis system communicatively coupled to the training system and the user testing platform, the computer system adapted to receive the user input responses generated in response to the current visual acuity test and to assign a visual acuity score for the testing platform user using the correlations obtained from the training system.

19. A system for a visual field test comprising, at least one data processor comprising a virtual reality, an augmented reality or a mixed reality engine and at least one memory storing instruction which is executed by at least one data processor, at least one data processor configured to:

(i) present a virtual assistant in virtual reality, augmented reality or mixed reality, wherein the virtual assistant presents to a patient a set of instructions for the visual field test, (ii) provide a set of n stimuli, wherein n is greater than or equal to 2, each stimulus having a (a) specified size, (b) shape and (c) luminance, wherein the luminance of the stimulus is greater than the luminance of a background;

(iii) receive from the patient at least one response when the patient views at least one stimulus, wherein the response comprises clicking the response button, a verbal response, a sound command or the objective analysis of the anterior segment of the eye;

(iv) repeat steps (ii) to (iii) at least y times, where y is greater than 2, until the patient indicates that the lowest stimulus intensity has been seen;

(v) repeat steps (i) to (iv), wherein the explanation in step (i) is modified based on the patient's response to provide a second set of instructions selected from a library of instructions if a percentage of responses in step (iii) labeled as correct is less than the percentage expected to be correct based on a historical value for the patient's retinal sensitivity score or an estimated percentage of correct choices based on a probability score; or (vi) calculate a visual field score if a percentage of responses in step (iii) labeled as correct is greater than or equal to the percentage expected to be correct based on a historical value for the patient's retinal sensitivity score or an estimated percentage of correct choices based on a probability score.

20. The system of implementation 19, further comprising a virtual reality, an augmented reality or a mixed reality headset.

21. The system of implementation 19, wherein the set of instructions comprises a patient guide or an explanation of the visual field test.

22. The system of implementation 19, wherein the virtual reality comprises augmented reality or mixed reality.

23. The system of implementation 19, wherein the set of instructions in step (i) further comprises noting the presentation of all the stimuli.

24. The system of implementation 23, wherein the set of instructions further comprises providing information to the patient on timing and sequence of the visual field test.

25. The system of implementation 19, wherein the set of instructions further comprises an explanation of responses of the patient.

26. The system of implementation 19, wherein the set of instructions comprises a verbal explanation.

27. The system of implementation 19, wherein the set of instructions comprises a pictorial explanation providing a set of actions and vector movements showing the position of the stimuli. (i) The stimulus blink and move indicating to the position of the stimulus.

(ii) The stimulus change their appearance by blinking, glowing, changing the color, hue or intensity to attract the attention of the patient being tested.

28. The system of implementation 19, wherein the virtual assistant uses eye-tracking to reposition the visual field stimulus matrix to avoid the effect of "fixation losses".

(i) The virtual assistant turns the eye-tracking cameras n milliseconds before showing a stimulus.

(ii) The virtual assistant uses the eye-tracking data to detect the actual gaze position.

virtual assistant changes the stimulus matrix to synchronize the center of the stimulus matrix with the actual optical axis or gaze position.

29. The system of implementation 19, wherein the virtual assistant is humanoid in appearance.

30. The system of implementation 19, wherein the virtual assistant is an avatar.

31. The system of implementation 19, wherein the virtual assistant is a cartoon character.

32. The system of implementation 19, wherein the virtual assistant is presented in two dimensions.

33. The system of implementation 19, wherein the virtual assistant is presented in three dimensions.

34. The system of implementation 19, wherein the virtual assistant is representational.

35. The system of implementation 19, wherein the stimulus are selected from the group consisting of circular stimuli of all Goldman sizes, sinusoidal bars and circular stimuli of different colors.

36. The system of implementation 19, wherein the virtual assistant uses neural networks (NN) and a decision tree to evaluate the inputs from patient, sensors and system state and provide a subsequent action.

37. The system of implementation 36, wherein neural networks and a decision tree are previously trained by:

(i) a training database, wherein the training database includes, for each member of a training population comprised of visual field tests taken by users, an assessment dataset that includes at least data relating to a respective user response to the visual field set and or a sensor input and or a system state.

(ii) a visual field score of the respective test; a training system including an expert system module configured to determine correlations between the respective user responses, sensor inputs and system state to the visual field test and the visual field score of each member of the training population.

(iii) a user testing platform configured to provide a user with a current visual field test and receive user input regarding responses to the current visual field test; an analysis system communicatively coupled to the training system and the user testing platform, the computer system adapted to receive the user input responses generated in response to the current visual field test and to assign a visual field score for the testing platform user using the correlations obtained from the training system.

38. A system for a contrast sensitivity test comprising, at least one data processor comprising a virtual reality, an augmented reality or a mixed reality engine and at least one memory storing instruction which is executed by at least one data processor, at least one data processor configured to:

(i) present a virtual assistant in virtual reality, augmented reality or mixed reality, wherein the virtual assistant presents to a patient a set of instructions for the contrast sensitivity test, (ii) provide a set of n optotypes, wherein n is greater than or equal to 2, each optotype having a (a) specified size, (b) shape and (c) luminance, wherein the luminance of the optotypes is greater than the luminance of a background;

(iii) receive from the patient at least one response when the patient views at least one optotype, wherein the response comprises selection of a position of the at least one optotype or location of an arrow associated with the at least one optotype;

(iv) repeat steps (ii) to (iii) at least y times, where y is greater than 2, until the patient indicates that he/she cannot identify any optotypes having a contrast lower than the last optotype the patient responded to in step (iii);

(v) repeat steps (i) to (iv), wherein the explanation in step (i) is modified based on the patient's response to provide a second set of instructions selected from a library instructions if a percentage of responses in step (iii) labeled as correct is less than the percentage expected to be correct based on a historical value for the patient's contrast sensitivity score or an estimated percentage of correct choices based on a probability score; or (vi) calculate a contrast sensitivity score if a percentage of responses in step (iii) labeled as correct is greater than or equal to the percentage expected to be correct based on a historical value for the patient's contrast sensitivity score or an estimated percentage of correct choices based on a probability score.

39. The system of implementation 38, further comprising a virtual reality, an augmented reality or a mixed reality headset.

40. The system of implementation 38, wherein the set of instructions comprises a patient guide or an explanation of the contrast sensitivity test.

41. The system of implementation 38, wherein the virtual reality comprises augmented reality or mixed reality.

42. The system of implementation 38, wherein the set of instructions in step (i) further comprises noting the location of the optotypes and the location of arrows in the test scenario.

43. The system of implementation 38, wherein the set of instructions further comprises providing information to the patient on timing and sequence of the contrast sensitivity test.

44. The system of implementation 38, wherein the set of instructions further comprises an explanation of responses of the patient.

45. The system of implementation 38, wherein the set of instructions comprises a verbal explanation.

46. The system of implementation 38, wherein the set of instructions comprises a pictorial explanation providing a set of actions and vector movements showing the position of the optotypes.

(i) The arrows blink and move indicating to the position of the optotype.

(ii) The optotypes change their appearance by blinking, glowing, changing the color, hue or intensity to attract the attention of the patient being tested.

47. The system of implementation 38, wherein the virtual assistant is humanoid in appearance.

48. The system of implementation 38, wherein the virtual assistant is an avatar.

49. The system of implementation 38, wherein the virtual assistant is a cartoon character.

50. The system of implementation 38, wherein the virtual assistant is presented in two dimensions.

51. The system of implementation 38, wherein the virtual assistant is presented in three dimensions.

52. The system of implementation 38, wherein the virtual assistant is representational.

53. The system of implementation 38, wherein the optotypes are selected from the group consisting of Sloan letters, Snellen E's, Landolt C's, ETDRS optotypes and Lea symbols or combinations of Lea symbols and letters for the pediatric population.

54. The system of implementation 38, wherein the virtual assistant uses neural networks (NN) and a decision tree to evaluate the inputs from patient, sensors and system state and provide a subsequent action.

55. The system of implementation 54, wherein neural networks and a decision tree are previously trained by:

(i) a training database, wherein the training database includes, for each member of a training population comprised of contrast sensitivity tests taken by users, an assessment dataset that includes at least data relating to a respective user response to the contrast sensitivity set and or a sensor input and or a system state.

(ii) a contrast sensitivity score of the respective test; a training system including an expert system module configured to determine correlations between the respective user responses, sensor inputs and system state to the contrast sensitivity test and the contrast sensitivity score of each member of the training population.

(iii) a user testing platform configured to provide a user with a current contrast sensitivity test and receive user input regarding responses to the current contrast sensitivity test; an analysis system communicatively coupled to the training system and the user testing platform, the computer system adapted to receive the user input responses generated in response to the current contrast sensitivity test and to assign a contrast sensitivity score for the testing platform user using the correlations obtained from the training system.

56. A system for a light adaptometry test comprising, at least one data processor comprising a virtual reality, an augmented reality or a mixed reality engine and at least one memory storing instruction which is executed by at least one data processor, at least one data processor configured to:

(i) present a virtual assistant in virtual reality, augmented reality or mixed reality, wherein the virtual assistant presents to a patient a set of instructions for the light adaptometry test, (ii) The patient is first light-adapted to a bright background light for a given time. Present a bright light to the patient to obtain photoreceptors saturation where the photopigments are scarce.

(iii) Present a set of n optotypes, wherein n is greater than or equal to 2, each optotype having a (a) specified size, (b) shape and (c) luminance, wherein the luminance of the optotypes is greater than the luminance of a background;

(iv) receive from the patient at least one response when the patient views at least one optotype, wherein the response comprises selection of a position of the at least one optotype or location of an arrow associated with the at least one optotype;

(v) repeat steps (ii) to (iii) at least y times, where y is greater than 2, until the patient indicates that he/she cannot identify any optotypes having a size smaller than the last optotype the patient responded to in step (iii);

(vi) repeat steps (i) to (iv), wherein the explanation in step (i) is modified based on the patient's response to provide a second set of instructions selected from a library of instructions if a percentage of responses in step (iii) labeled as correct is less than the percentage expected to be correct based on a historical value for the patient's visual acuity score or an estimated percentage of correct choices based on a probability score; or (vii) calculate the time it takes for a patient to perceive the optotypes after the light adaptation;

(viii) calculate a visual acuity score if a percentage of responses in step (iii) labeled as correct is greater than or equal to the percentage expected to be correct based on a historical value for the patient's visual acuity score or an estimated percentage of correct choices based on a probability score.

57. The system of implementation 56, further comprising a virtual reality, an augmented reality or a mixed reality headset.

58. The system of implementation 56, wherein the set of instructions comprises a patient guide or an explanation of the light adaptation also called adaptometry test.

59. The system of implementation 56, wherein the virtual reality comprises augmented reality or mixed reality.

60. The system of implementation 56, wherein the set of instructions in step (i) further comprises noting the location of the optotypes and the location of arrows in the test scenario.

61. The system of implementation 60, wherein the set of instructions further comprises providing information to the patient on timing and sequence of the adaptometry test.

62. The system of implementation 56, wherein the set of instructions further comprises an explanation of responses of the patient.

63. The system of implementation 56, wherein the set of instructions comprises a verbal explanation.

64. The system of implementation 56, wherein the set of instructions comprises a pictorial explanation providing a set of actions and vector movements showing the position of the optotypes.
  (i) The arrows blink and move indicating to the position of the optotype.
  (ii) The optotypes change their appearance by blinking, glowing, changing the color, hue or intensity to attract the attention of the patient being tested.

65. The system of implementation 56, wherein the virtual assistant is humanoid in appearance.

66. The system of implementation 56, wherein the virtual assistant is an avatar.

67. The system of implementation 56, wherein the virtual assistant is a cartoon character.

68. The system of implementation 56, wherein the virtual assistant is presented in two dimensions.

69. The system of implementation 56, wherein the virtual assistant is presented in three dimensions.

70. The system of implementation 56, wherein the virtual assistant is representational.

71. The system of implementation 56, wherein the optotypes are selected from the group consisting of Sloan letters, Snellen E's, Landolt C's, ETDRS optotypes and Lea symbols or combinations of Lea symbols and letters for the pediatric population.

72. The system of implementation 56, wherein the virtual assistant uses neural networks (NN) and a decision tree to evaluate the inputs from patient, sensors and system state and provide a subsequent action.

73. The system of implementation 72, wherein neural networks and a decision tree are previously trained by:
  (i) a training database, wherein the training database includes, for each member of a training population comprised of light adaptometry tests taken by users, an assessment dataset that includes at least data relating to a respective user response to the light adaptometry set and or a sensor input and or a system state.
  (ii) a light adaptometry score of the respective test; a training system including an expert system module configured to determine correlations between the respective user responses, sensor inputs and system state to the light adaptometry test and the light adaptometry score of each member of the training population.
  (iii) a user testing platform configured to provide a user with a current light adaptometry test and receive user input regarding responses to the current light adaptometry test; an analysis system communicatively coupled to the training system and the user testing platform, the computer system adapted to receive the user input responses generated in response to the current light adaptometry test and to assign a light adaptometry score for the testing platform user using the correlations obtained from the training system.

74. A system for a tonometry test comprising,
  at least one data processor comprising a virtual reality, an augmented reality or a mixed reality engine and at least one memory storing instruction which is executed by at least one data processor, at least one data processor configured to:
    present a virtual assistant in virtual reality, augmented reality or mixed reality, wherein the virtual assistant presents to a patient a set of instructions for the tonometry test,
    (ii) The patient is first presented a series of videos showing the visual perception of the tonometry from the patient's eyes perspective.
    The patient is presented a group of verbal explanation of the tonometry test.
    A set of instructions further comprises providing information to the patient on timing and sequence of the tonometry test.

75. The system of implementation 74, further comprising a virtual reality, an augmented reality or a mixed reality headset.

76. The system of implementation 74, wherein the tonometry test comprises but not limited to indentation tonometry, applanation tonometry.

77. The system of implementation 74, wherein the virtual reality comprises augmented reality or mixed reality.

78. The system of implementation 74, wherein the set of instructions comprises a verbal explanation.

79. The system of implementation 74, wherein the set of instructions comprises a pictorial explanation providing a set of actions and vector movements showing the position of the tonometer.

80. The system of implementation 74, wherein the virtual assistant is humanoid in appearance.

81. The system of implementation 74, wherein the virtual assistant is an avatar.

82. The system of implementation 74, wherein the virtual assistant is a cartoon character.

83. The system of implementation 74, wherein the virtual assistant is presented in two dimensions.

84. The system of implementation 74, wherein the virtual assistant is presented in three dimensions.

85. The system of implementation 74, wherein the virtual assistant is representational.

86. A system for a color test comprising,
  at least one data processor comprising a virtual reality, an augmented reality or a mixed reality engine and at least one memory storing instruction which is executed by at least one data processor, at least one data processor configured to:
    (i) present a virtual assistant in virtual reality, augmented reality or mixed reality, wherein the virtual assistant presents to a patient a set of instructions for the color test,
    (ii) provide a set of n optotypes, wherein n is greater than or equal to 2, each optotype having a (a) specified size, (b) shape and (c) luminance, wherein the luminance of the optotypes is similar to the luminance of a background;
    (iii) receive from the patient at least one response when the patient views at least one optotype, wherein the response comprises selection of a position of the at least one optotype or location of an arrow associated with the at least one optotype;
    (iv) repeat steps (ii) to (iii) at least y times, where y is greater than 2, until the patient indicates that he/she cannot identify any optotypes having a hue lower than the last optotype the patient responded to in step (iii);
    (v) repeat steps (i) to (iv), wherein the explanation in step (i) is modified based on the patient's response to provide a second set of instructions selected from a library instructions if a percentage of responses in step (iii) labeled as correct is less than the percentage expected to be correct based on a historical value for the patient's color score or an estimated percentage of correct choices based on a probability score; or (vi) calculate a color sensitivity score if a percentage of responses in step (iii) labeled as correct is greater than or equal to the percentage expected to be correct based on a historical value for the patient's color sensitivity score or an estimated percentage of correct choices based on a probability score.

(vii) the color test comprises a Farnsworth-Munsell 100 Hue Color Vision Test, a Farnsworth-Munsell 15 Hue Color Vision Test or Ishihara color test.

87. The system of implementation 86, further comprising a virtual reality, an augmented reality or a mixed reality headset.

88. The system of implementation 86, wherein the set of instructions comprises a patient guide or an explanation of the color test.

89. The system of implementation 86, wherein the virtual reality comprises augmented reality or mixed reality.

90. The system of implementation 86, wherein the set of instructions in step (i) further comprises noting the location of the optotypes and the location of arrows in the test scenario.

91. The system of implementation 90, wherein the set of instructions further comprises providing information to the patient on timing and sequence of the color test.

92. The system of implementation 86, wherein the set of instructions further comprises an explanation of responses of the patient.

93. The system of implementation 86, wherein the set of instructions comprises a verbal explanation.

94. The system of implementation 86, wherein the set of instructions comprises a pictorial explanation providing a set of actions and vector movements showing the position of the optotypes:
(i) The arrows blink and move indicating to the position of the optotype; and
(ii) The optotypes change their appearance by blinking, glowing, changing the color, hue or intensity to attract the attention of the patient being tested.

95. The system of implementation 86, wherein the virtual assistant is humanoid in appearance.

96. The system of implementation 86, wherein the virtual assistant is an avatar.

97. The system of implementation 86, wherein the virtual assistant is a cartoon character.

98. The system of implementation 86, wherein the virtual assistant is presented in two dimensions.

99. The system of implementation 86, wherein the virtual assistant is presented in three dimensions.

100. The system of implementation 86, wherein the virtual assistant is representational.

101. The system of implementation 86, wherein the optotypes are selected from the group consisting of Sloan letters, Snellen E's, Landolt C's, ETDRS optotypes and Lea symbols or combinations of Lea symbols and letters for the pediatric population.

102. The system of implementation 86, wherein the virtual assistant uses neural networks (NN) and a decision tree to evaluate the inputs from patient, sensors and system state and provide a subsequent action.

103. The system of implementation 102, wherein neural networks and a decision tree are previously trained by:

(i) a training database, wherein the training database includes, for each member of a training population comprised of color vision tests taken by users, an assessment dataset that includes at least data relating to a respective user response to the color vision set and or a sensor input and or a system state.

(ii) a color vision score of the respective test; a training system including an expert system module configured to determine correlations between the respective user responses, sensor inputs and system state to the color vision test and the color vision score of each member of the training population.

(iii) a user testing platform configured to provide a user with a current color vision test and receive user input regarding responses to the current color vision test; an analysis system communicatively coupled to the training system and the user testing platform, the computer system adapted to receive the user input responses generated in response to the current color vision test and to assign a color vision score for the testing platform user using the correlations obtained from the training system.

104. A system for ophthalmic photography comprising, at least one data processor comprising a virtual reality, an augmented reality or a mixed reality engine and at least one memory storing instruction which is executed by at least one data processor, at least one data processor configured to:
(i) present a virtual assistant in virtual reality, augmented reality or mixed reality, wherein the virtual assistant presents to a patient a set of instructions for the ophthalmic photography,
(ii) provide a set of fixation methods having a (a) specified size, (b) shape and (c) luminance, wherein the luminance of the fixation is greater to the luminance of a background;
(iii) receive from the patient at least one response when the patient views at least one fixation method, wherein the response comprises selection of a position of the at least one fixation method or location of an arrow associated with the at least one fixation method;
(iv) repeat steps (i) to (iii), wherein the explanation in step (i) is modified based on the patient's response to provide a second set of instructions selected from a library.

105. The system of implementation 104, further comprising a virtual reality, an augmented reality or a mixed reality headset.

106. The system of implementation 104, wherein the set of instructions comprises a patient guide or an explanation of the ophthalmic photography.

107. The system of implementation 104, wherein the virtual reality comprises augmented reality or mixed reality.

108. The system of implementation 106, wherein the set of instructions further comprises providing information to the patient on timing and sequence of the ophthalmic photography.

109. The system of implementation 104, wherein the set of instructions comprises a verbal explanation.

110. The system of implementation 104, wherein the set of instructions comprises a pictorial explanation providing a set of actions and vector movements showing the position of the fixation methods.
(i) The arrows blink and move indicating to the position of the fixation method.
(ii) The fixation method change their appearance by blinking, glowing, changing the color, hue or intensity to attract the attention of the patient being tested.

111. The system of implementation 104, wherein the virtual assistant is humanoid in appearance.

112. The system of implementation 104, wherein the virtual assistant is an avatar.

113. The system of implementation 104, wherein the virtual assistant is a cartoon character.

114. The system of implementation 104, wherein the virtual assistant is presented in two dimensions.

115. The system of implementation 104, wherein the virtual assistant is presented in three dimensions.

116. The system of implementation 104, wherein the virtual assistant is representational.

117. The system of implementation 104, wherein the testing platform configured to provide a user with a current ophthalmic photography and receive user input regarding the quality of the photograph.

118. The system of implementation 104, wherein the ophthalmic photography comprises a color analog photography or a scanning laser ophthalmoscope or infrared photography.

119. The system of implementation 104, wherein the ophthalmic photography comprises a fundus photography; photography of the posterior segment of the eye; photography of the anterior segment of the eye; photography of the adnexa of the eye.

120. A system for a color test comprising,
at least one data processor comprising a virtual reality, an augmented reality or a mixed reality engine and at least one memory storing instruction which is executed by at least one data processor, at least one data processor configured to:
(i) present a virtual assistant in virtual reality, augmented reality or mixed reality, wherein the virtual assistant presents to a patient a set of instructions for the gaze alignment test,
(ii) provide a set of n targets, wherein n is greater than or equal to 2, each target having a (a) specified size, (b) shape and (c) luminance, wherein the luminance of the target is greater to the luminance of a background;
(iii) receive from the patient at least one response when the patient views at least one target, wherein the response comprises selection of a position of the at least one target or location of an arrow associated with the at least one target;
(iv) the targets move in predefined directions on the screen and the virtual assistant instructs the patient to follow the moving targets.
(v) repeat steps (i) to (iv), wherein the explanation in step (i) is modified based on the patient's response to provide a second set of instructions selected from a library of instructions if the eye movements in step (iv) is labeled as less than the percentage expected to be correct based on a historical value for the patient's eye movement ranges or an estimated percentage of correct choices based on a healthy probability; or
(vi) calculate a movement range amplitude and label it as correct if greater than or equal to the percentage expected to be correct based on a historical value for the patient's eye movement ranges or an estimated percentage of correct choices based on a probability score.

121. The system of implementation 120, further comprising a virtual reality, an augmented reality or a mixed reality headset.

122. The system of implementation 120, wherein the set of instructions comprises a patient guide or an explanation of the eye alignment test.

123. The system of implementation 120, wherein the virtual reality comprises augmented reality or mixed reality.

124. The system of implementation 120, wherein the set of instructions in step (i) further comprises following the location of the targets and the location of arrows in the test scenario.

125. The system of implementation 120, wherein the set of instructions further comprises providing information to the patient on timing and sequence of the eye alignment test.

126. The system of implementation 120, wherein the set of instructions further comprises an explanation of responses of the patient.

127. The system of implementation 120, wherein the set of instructions comprises a verbal explanation.

128. The system of implementation 120, wherein the set of instructions comprises a pictorial explanation providing a set of actions and vector movements showing the position of the targets.
(i) The arrows blink and move indicating to the position of the target.
(ii) The targets change their appearance by blinking, glowing, changing the color, hue or intensity to attract the attention of the patient being tested.

129. The system of implementation 120, wherein the virtual assistant is humanoid in appearance.

130. The system of implementation 120, wherein the virtual assistant is an avatar.

131. The system of implementation 120, wherein the virtual assistant is a cartoon character.

132. The system of implementation 120, wherein the virtual assistant is presented in two dimensions.

133. The system of implementation 120, wherein the virtual assistant is presented in three dimensions.

134. The system of implementation 120, wherein the virtual assistant is representational.

135. The system of implementation 120, wherein the eye alignment test comprises a cover test; ocular range of motion; tropias and phorias test; corneal light reflects test; strabismus test; eye misalignment test; esotropia, exotropia, hypertropia, hypotropia test; esophoria, exophoria, hyperphoria, hypophoria test and/or Hirschberg test.

136. The system of implementation 120, wherein the virtual assistant uses neural networks (NN) and a decision tree to evaluate the inputs from patient, sensors and system state and provide a subsequent action.

137. The system of implementation 136, wherein neural networks and a decision tree are previously trained by:
(i) a training database, wherein the training database includes, for each member of a training population comprised of eye alignment tests taken by users, an assessment dataset that includes at least data relating to a respective user response to the eye alignment set and or a sensor input and or a system state.
(ii) an eye alignment score of the respective test; a training system including an expert system module configured to determine correlations between the respective user responses, sensor inputs and system state to the eye alignment test and the eye alignment score of each member of the training population.
(iii) a user testing platform configured to provide a user with a current eye alignment test and receive user input regarding responses to the current eye alignment test; an analysis system communicatively coupled to the training system and the user testing platform, the computer system adapted to receive the user input responses generated in response to the current eye alignment test and to assign a eye alignment score for the testing platform user using the correlations obtained from the training system.

Pupillometry

138. A system for pupillometry test comprising,
at least one data processor comprising a virtual reality, an augmented reality or a mixed reality engine and at least one memory storing instruction which is executed by at least one data processor, at least one data processor configured to:
(i) present a virtual assistant in virtual reality, augmented reality or mixed reality, wherein the virtual assistant presents to a patient a set of instructions for the pupillometry test,
(ii) provide a set of fixation methods having a (a) specified size, (b) shape and (c) luminance, wherein the luminance of the fixation is greater to the luminance of a background;
(iii) receive from the patient at least one response when the patient views at least one fixation method, wherein the response comprises selection of a position of the at least one fixation method or location of an arrow associated with the at least one fixation method;
repeat steps (i) to (iii), wherein the explanation in step (i) is modified based on the patient's response to provide a second set of instructions selected from a library.

Present a series of luminance stimulus and record the pupil response.

139. The system of implementation 138, further comprising a virtual reality, an augmented reality or a mixed reality headset.

140. The system of implementation 138, wherein the set of instructions comprises a patient guide or an explanation of the pupillometry test.

141. The system of implementation 140, wherein the set of instructions further comprises providing information to the patient on timing and sequence of the pupillometry test.

142. The system of implementation 138, wherein the set of instructions comprises a verbal explanation.

143. The system of implementation 138, wherein the set of instructions comprises a pictorial explanation providing a set of actions and vector movements showing the position of the fixation methods.
(i) The arrows blink and move indicating to the position of the fixation method.
(ii) The fixation method changes their appearance by blinking, glowing, changing the color, hue or intensity to attract the attention of the patient being tested.

144. The system of implementation 138, wherein the virtual assistant is humanoid in appearance.

145. The system of implementation 138, wherein the virtual assistant is an avatar.

146. The system of implementation 138, wherein the virtual assistant is a cartoon character.

147. The system of implementation 138, wherein the virtual assistant is presented in two dimensions.

148. The system of implementation 138, wherein the virtual assistant is presented in three dimensions.

149. The system of implementation 138, wherein the virtual assistant is representational.

150. The system of implementation 138, wherein the testing platform configured to provide a user with a current pupillometry test and receive user input regarding the quality of the pupillometry test.

151. The system of implementation 138, wherein the pupillometry test comprises a video pupillography; a focal pupillometry; global or diffuse pupillometry; multifocal pupillometry test, an achromatic or a chromatic pupillometry test.

Autorefraction

152. A system for autorefraction test comprising,
at least one data processor comprising a virtual reality, an augmented reality or a mixed reality engine and at least one memory storing instruction which is executed by at least one data processor, at least one data processor configured to:
(i) present a virtual assistant in virtual reality, augmented reality or mixed reality, wherein the virtual assistant presents to a patient a set of instructions for the autorefraction test,
(ii) provide a set of fixation methods having a (a) specified size, (b) shape and (c) luminance, wherein the luminance of the fixation is greater or lower than the luminance of a background;
(iii) receive from the patient at least one response when the patient views at least one fixation method, wherein the response comprises selection of a position of the at least one fixation method or location of an arrow associated with the at least one fixation method;
repeat steps (i) to (iii), wherein the explanation in step (i) is modified based on the patient's response to provide a second set of instructions selected from a library.

Present a series of targets with different focal points and the patient interact with the assistant to let the system know if the patient is perceiving the target changes.

153. The system of implementation 152, further comprising a virtual reality, an augmented reality or a mixed reality headset.

154. The system of implementation 152, wherein the set of instructions comprises a patient guide or an explanation of the autorefraction test.

155. The system of implementation 154, wherein the set of instructions further comprises providing information to the patient on timing and sequence of the autorefraction test.

156. The system of implementation 152, wherein the set of instructions comprises a verbal explanation.

157. The system of implementation 152, wherein the set of instructions comprises a pictorial explanation providing a set of actions and vector movements showing the position of the fixation methods.
(i) The arrows blink and move indicating to the position of the fixation method.
(ii) The fixation method changes their appearance by blinking, glowing, changing the color, hue or intensity to attract the attention of the patient being tested.

158. The system of implementation 152, wherein the virtual assistant is humanoid in appearance.

159. The system of implementation 152, wherein the virtual assistant is an avatar.

160. The system of implementation 152, wherein the virtual assistant is a cartoon character.

161. The system of implementation 152, wherein the virtual assistant is presented in two dimensions.

162. The system of implementation 152, wherein the virtual assistant is presented in three dimensions.

163. The system of implementation 152, wherein the virtual assistant is representational.

164. The system of implementation 152, wherein the testing platform configured to provide a user with a current autorefraction test and receive user input regarding the quality of the autorefraction test.

Vision Therapy, Electromagnetic and Light Treatment

165. A system for Vision therapy, electromagnetic and light treatment comprising, at least one data processor comprising a virtual reality, an augmented reality or a mixed reality engine and at least one memory storing instruction which is executed by at least one data processor, at least one data processor configured to:
(i) present a virtual assistant in virtual reality, augmented reality or mixed reality, wherein the virtual assistant presents to a patient a set of instructions for the Vision therapy, electromagnetic and light treatment,
(ii) provide a set of fixation methods having a (a) specified size, (b) shape and (c) luminance, wherein the luminance of the fixation is greater or lower than the luminance of a background;
(iii) receive from the patient at least one response when the patient views at least one fixation method, wherein the response comprises selection of a position of the at least one fixation method or location of an arrow associated with the at least one fixation method;
repeat steps (i) to (iii), wherein the explanation in step (i) is modified based on the patient's response to provide a second set of instructions selected from a library;
Present a series of luminance stimulus and record the pupil response.
Present a series of electromagnetic stimulus and record the pupil response.

166. The system of implementation 165, further comprising a virtual reality, an augmented reality or a mixed reality headset.

167. The system of implementation 165, wherein the set of instructions comprises a patient guide or an explanation of the Vision therapy, electromagnetic and light treatment.

168. The system of implementation 167, wherein the set of instructions further comprises providing information to the patient on timing and sequence of the Vision therapy, electromagnetic and light treatment.

169. The system of implementation 165, wherein the set of instructions comprises a verbal explanation.

170. The system of implementation 165, wherein the set of instructions comprises a pictorial explanation providing a set of actions and vector movements showing the position of the fixation methods.
(i) The arrows blink and move indicating to the position of the fixation method;
(ii) The fixation method changes their appearance by blinking, glowing, changing the color, hue or intensity to attract the attention of the patient being tested.

171. The system of implementation 165, wherein the virtual assistant is humanoid in appearance.

172. The system of implementation 165, wherein the virtual assistant is an avatar.

173. The system of implementation 165, wherein the virtual assistant is a cartoon character.

174. The system of implementation 165, wherein the virtual assistant is presented in two dimensions.

175. The system of implementation 165, wherein the virtual assistant is presented in three dimensions.

176. The system of implementation 165, wherein the virtual assistant is representational.

177. A head-mounted system for conducting visual tests of a subject, the head-wearable device comprising: a head-mounted display device configured to provide a visual test to the subject; at least one subject sensor configured to monitor the subject during administration of the visual test; a processor, configured by code executing therein to: cause the head-mounted display device to display one of a plurality of pre-determined visual tests to the subject, wherein each of the plurality of pre-determined visual tests includes one or more operational states and at least one virtual assistant provided within a visual field displayed to the subject; while administering one of a plurality of pre-determined visual tests, provide the output of the at least one subject sensor and a current operational state of the displayed one of a plurality of visual tests to a pre-trained neural network, wherein the pre-trained neural network is configured to output an instruction set in response to the current operational state and the sensor output; wherein the instruction set causes the virtual assistant to provide one or more action prompts to the subject that instructs the subject to a corrective physical action during administration of the visual test.

178. The system of implementation 177, wherein the visual test is selected from: visual field test, visual acuity test, contrast sensitivity test, light adaptometry test, tonometry test, ophthalmic phototherapy test; pupillometry test; autorefraction test; and visual therapy.

179. A method of administering a visual test to a subject, the method comprising: providing one of a plurality of visual tests, each visual test having a plurality of operational states, to a display device incorporated within a head-mounted device, the display device configured to provide a virtual reality scene to the subject; receiving sensor data from one or more sensors disposed within the head mounted device, wherein at least one sensor is configured to track the eye-movements of the subject; generating a virtual assist avatar within the virtual reality scene displayed to the subject; providing the received sensor data and current operational state of the displayed one of a plurality of visual tests to a pre-trained neural network, wherein the pre-trained neural network is configured to correlate the sensor and operation state input values with an instruction set, wherein the instruction set includes one or more audiovisual prompts for display by the virtual assistant; and receiving the instruction set and causing the virtual assistant to provide the one or more audiovisual action prompts to the subject, wherein the audiovisual action prompt is correlated with a correction action that instructs the subject to a corrective physical action during administration of the visual test.

180. The system of any of the previous implementations, wherein the pre-trained neural network are trained by: (i) providing a first training dataset to a first neural network, wherein the training dataset is stored in a training database, wherein the training dataset includes, for each member of a training population comprised of users of one or more visual tests, an assessment dataset that includes at least data relating to at least one sensor measurement of a respective user in response to an operational state of the visual test; wherein the operation state includes at least a success state and a fail state; (ii) training the first neural network to determine correlations between the respective assessment data set and the operational state of the visual test for each member of the training population; (iii) providing a second neural network with a second training data set, wherein the second training data set includes one of a plurality of pre-determined operational states of the visual test and one or more corrective subject instructions to change a fail state to a success state; (iv) training the second neural network to determine correlations between the operational state of the visual test and the corrective instructions to change fail states to success states; (v) training a third neural network by providing the assessment data to the first neural network, and providing the output of the first neural network to the second neural network as an input, so as to determine the correlation between the assessment dataset and a corrective action to change an associated fail operational state; (vi) outputting the third neural network as a trained neural network.

181. Wherein the set of instructions provided to the wearer of the virtual reality or mixed reality goggles in any of the foregoing implementations includes a pre-determined explanation of responses of the wearer selected in response to data obtained from the processor.

182. Wherein in any of the foregoing implementations the pictorial explanation is provided by a dynamically generated virtual assistant, the processor is configured to use real-time eye-tracking to reposition the visual field stimulus matrix to avoid the effect of fixation losses, wherein the repositioning includes: (i) turning the eye-tracking cameras n milliseconds before showing a stimulus; (ii) using the eye-tracking data to detect the actual gaze position; and changing the stimulus matrix to synchronize the center of the stimulus matrix with the actual optical axis or gaze position.

183. Wherein in any of the foregoing implementations a virtual assistant is provided, the virtual assistant is depicted as a photorealistic avatar.

While this specification contains many specific embodiment details, these should not be construed as limitations on the scope of any embodiment or of what can be claimed, but rather as descriptions of features that can be specific to particular embodiments of particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features can be described above as acting in certain combinations and even initially claimed as such, one or more features from a claimed combination can in some cases be excised from the combination, and the claimed combination can be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing can be advantageous. Moreover, the separation of various system components in the embodiments described above should not be understood as requiring such separation in all embodiments, and it should be understood that the described program components and systems can generally be integrated together in a single software product or packaged into multiple software products.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components, and/or groups thereof.

It should be noted that use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Particular embodiments of the subject matter described in this specification have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain embodiments, multitasking and parallel processing can be advantageous.

Publications and references to known registered marks representing various systems are cited throughout this application, the disclosures of which are incorporated herein by reference. Citation of any above publications or documents is not intended as an admission that any of the foregoing is pertinent prior art, nor does it constitute any admission as to the contents or date of these publications or documents. All references cited herein are incorporated by reference to the same extent as if each individual publication and references were specifically and individually indicated to be incorporated by reference.

While the invention has been particularly shown and described with reference to a preferred embodiment thereof, it will be understood by those skilled in the art that various changes in form and details may be made therein without departing from the spirit and scope of the invention. As such, the invention is not defined by the discussion that appears above, but rather is defined by the claims that follow, the respective features recited in those points, and by equivalents of such features.

What is claimed is:

1. A system to administer a plurality of simultaneous and separate Visual Field Tests for both eyes to at least one user, wherein the system includes a wearable display device, said wearable display device comprising:
   a display portion comprising a screen divided into two halves by a divider or a set of at least two screens that restricts views presented to each eye of the at least one user;
   a plurality of sensors comprising at least an infra-red (IR)-based eye tracking sensor configured to track a position of each eye of the at least one user;
   one or more processors; and
   a memory having stored thereon machine-readable instructions that cause, when executed, said one or more processors to:
   (i) conduct a strabismus test by:
      I) presenting a virtual assistant in virtual reality, augmented reality or mixed reality, wherein the virtual assistant presents to the at least one user a set of instructions for the strabismus test,
      II) providing a set of m targets, wherein m is greater than or equal to 2, each target having a (a) specified size, (b) shape and (c) luminance, wherein the luminance of the target is greater to the luminance of a background, and wherein the stimuli alternate between the two halves or the at least two screens of the display portion so as to be visible only to each respective eye of the at least one user;
      III) calculating a movement range amplitude for each eye of the at least one user according to the position of each eye tracked based on IR signals detected using the IR-based eye tracking sensor;

VIII) determining that the at least one user suffers from strabismus when the calculated movement range amplitude is less than an estimated percentage based on a healthy probability;

(ii) upon determining that the at least one user suffers from strabismus based on the strabismus test, show a respective fixation target on each of the two halves or the at least two screens simultaneously where both eyes of the at least one user can see the respective fixation targets as one single fixation target;

(ii) provide a set of n stimuli, wherein n is greater than or equal to 2, each stimulus having a (a) specified size, (b) shape and (c) luminance, wherein the luminance of each stimulus is greater than the luminance of the background, and wherein the stimuli alternate between the two halves or the at least two screens of the display portion so as to be visible only to each respective eye of the at least one user while maintaining the fixation targets on both halves or screens to be seen as the one single fixation target by both eyes of the at least one user;

(iii) receive, from the at least one user, at least one response corresponding to at least one stimulus;

(iv) repeat steps (ii) to (iii) at least y times, where y is greater than 2, until the at least one user indicates that a lowest stimulus intensity has been seen; and (vii) calculate a visual field score if a percentage of responses in step (iii) labeled as correct is greater than or equal to the percentage expected to be correct based on a historical value for a retinal sensitivity score associated with the at least one user or an estimated percentage of correct choices based on a probability score, wherein the wearable display device comprises at least one tracking sensor, the at least one tracking sensor is configured to track eye-movements of the at least one user, and said one or more processors are further adapted to determine whether the at least one response received at step (iii) contains an error by the at least one user based on one or more corresponding responses from the at least one tracking sensor, wherein the processor, upon determining the at least one response received at step (iii) contains an error by the at least one user, is further adapted to:

automatically pause the visual field test; and display an explanation of the user error on the display portion.

2. The system of claim 1 wherein:
(i) the wearable display device is one of a virtual, augmented and mixed reality goggles device configured to provide a visual test to a wearer;
(ii) the wearable display device comprises at least one subject sensor configured to monitor the at least one user during administration of the visual test;
(iii) the wearable display device comprises at least one data processor and at least one memory storing; and
(v) the at least one tracking sensor is disposed within the goggles.

3. The system of claim 1, wherein step (i) further comprises presenting a set of instructions comprising a patient guide or an explanation of the visual field test.

4. The system of claim 1, wherein step (i) further comprises presenting a virtual reality that comprises augmented reality or mixed reality.

5. The system of claim 1, wherein step (i) further comprises presenting a set of instructions noting a presentation of all stimuli.

6. The system of claim 5, wherein the set of instructions further comprises providing information to the at least one user on timing and sequence of the visual field test.

7. The system of claim 6, wherein the set of instructions further comprises a predetermined explanation of responses of the at least one user selected in response to data obtained from the processor.

8. The system of claim 7, wherein the set of instructions comprises a verbal explanation.

9. The system of claim 5, wherein the set of instructions comprises a pictorial explanation providing a set of actions and vector movements showing a position of a stimulus, wherein:
(i) a stimulus blinks and moves indicating to a position of the stimulus; and
(ii) the stimulus changes appearance by blinking, glowing, changing a color, hue or intensity to attract attention from the at least one user being tested.

10. The system of claim 9, wherein the pictorial explanation is provided by a dynamically generated virtual assistant and the processor is configured to use real-time eye-tracking to reposition a visual field stimulus matrix to avoid the effect of fixation losses, wherein the repositioning includes:
(i) turning eye-tracking cameras n milliseconds before showing a stimulus;
(ii) using eye-tracking data to detect an actual gaze position; and
(iii) changing the visual field stimulus matrix to synchronize a center of the visual field stimulus matrix with an actual optical axis or gaze position.

11. The system of claim 10, wherein the virtual assistant is humanoid in appearance.

12. The system of claim 10, wherein the virtual assistant is a photorealistic avatar.

13. The system of claim 10, wherein the virtual assistant is a cartoon character.

14. The system of claim 10, wherein the virtual assistant is presented in three dimensions.

15. The system of claim 1, wherein the stimuli are selected from the group consisting of: circular stimuli of all Goldman sizes, sinusoidal bars, and circular stimuli of different colors.

16. The system of claim 1, wherein the one or more processors use artificial neural networks (NN) and a decision tree to evaluate inputs from the at least one user, sensors and system state and provide a subsequent action, wherein the neural network and decision tree are trained by:
(i) a training database, wherein the training database includes, for each member of a training population comprised of visual field tests taken by users, an assessment dataset that includes at least data relating to a respective user response to one or more of the visual field test, a sensor input, and a system state;
(ii) a visual field score of each respective test; a training system including an expert system module configured to determine correlations between respective user responses, sensor inputs, and system state to the visual field test and a visual field score of each member of a training population;
(iii) a user testing platform configured to provide a user with a current visual field test and receive user input regarding responses to the current visual field test; an analysis system communicatively coupled to the training system and the user testing platform, the analysis system adapted to receive user input responses generated in response to a current visual field test and to assign a visual field score for a testing platform user using correlations obtained from the training system.

17. The system of claim 16, wherein a pre-trained neural network is trained by:
  (i) providing a first training dataset to a first neural network, wherein the first training dataset is stored in the training database, wherein the first training dataset includes, for each member of the training population comprised of users of one or more visual tests, an assessment dataset that includes at least data relating to at least one sensor measurement of a respective user in response to an operational state of the visual test; wherein the operational state includes at least a success state and a fail state;
  (ii) training the first neural network to determine correlations between the respective assessment data set and the operational state of the visual test for each member of the training population;
  (iii) providing a second neural network with a second training data set, wherein the second training data set includes one of a plurality of pre-determined operational states of the visual test and one or more corrective subject instructions to change a fail state to a success state;
  iv) training the second neural network to determine correlations between the operational state of the visual test and the corrective instructions to change fail states to success states;
  (v) training a third neural network by providing the assessment data to the first neural network, and providing the output of the first neural network to the second neural network as an input, so as to determine the correlation between the assessment dataset and a corrective action to change an associated fail operational state; and
  (vi) outputting the third neural network as a trained neural network.

* * * * *